United States Patent
Hu et al.

(10) Patent No.: US 8,940,723 B2
(45) Date of Patent: Jan. 27, 2015

(54) COMBINATION OF A PYRROLOQUINOLINE COMPOUND AND A BETA-LACTAM ANTIMICROBIAL AGENT, MUPIROCIN OR CHLORHEXIDINE

(75) Inventors: Yanmin Hu, London (GB); Anthony R. M. Coates, London (GB)

(73) Assignee: Helperby Therapeutics Limited, London (GB)

( * ) Notice: Subject to any disclaimer, the term of this patent is extended or adjusted under 35 U.S.C. 154(b) by 0 days.

(21) Appl. No.: 13/814,191

(22) PCT Filed: Aug. 5, 2011

(86) PCT No.: PCT/GB2011/001181
§ 371 (c)(1),
(2), (4) Date: Mar. 25, 2013

(87) PCT Pub. No.: WO2012/017215
PCT Pub. Date: Feb. 9, 2012

(65) Prior Publication Data
US 2013/0184230 A1    Jul. 18, 2013

(30) Foreign Application Priority Data

Aug. 5, 2010 (GB) .................................. 1013209.0
Aug. 5, 2010 (GB) .................................. 1013212.4
Aug. 5, 2010 (GB) .................................. 1013214.0

(51) Int. Cl.
| | | |
|---|---|---|
| *A01N 55/02* | (2006.01) | |
| *A61K 31/555* | (2006.01) | |
| *A61K 31/43* | (2006.01) | |
| *A61K 31/351* | (2006.01) | |
| *A61K 31/155* | (2006.01) | |
| *A61K 31/4745* | (2006.01) | |
| *A61K 45/06* | (2006.01) | |
| *A61K 31/7036* | (2006.01) | |
| *A61K 31/424* | (2006.01) | |

(52) U.S. Cl.
CPC ............. *A61K 31/4745* (2013.01); *A61K 31/43* (2013.01); *A61K 31/351* (2013.01); *A61K 31/155* (2013.01); *A61K 45/06* (2013.01); *A61K 31/7036* (2013.01); *A61K 31/424* (2013.01)
USPC ........... 514/187; 514/183; 514/184; 514/185; 514/186

(58) Field of Classification Search
None
See application file for complete search history.

(56) References Cited

FOREIGN PATENT DOCUMENTS

| WO | WO 2007/054693 A1 | 5/2007 |
| WO | WO 2008/056151 A1 | 5/2008 |

OTHER PUBLICATIONS

Hu, Y. et al: "A new approach for the discovery of antibiotics by targeting non-multiplying bacteria: A novel topical antibiotic for Staphylococcal infections", PLOS ONE 2010 Public Library of Science USA LNKD- DOI: 10.1371/Journal.Pone.0011818, vol. 5, No. 7, Jul. 2010.

*Primary Examiner* — Patrick Lewis
(74) *Attorney, Agent, or Firm* — Steptoe & Johnson LLP

(57) ABSTRACT

This invention relates to the use of 4-methyl-8-phenoxy-1-(2-phenylethyl)-2,3-dihydro-1H-pyrrolo[3,2-c]quinoline or a pharmaceutically acceptable derivative thereof in combination with another antimicrobial agent selected from the group consisting of a beta-lactam antimicrobial agent, mupirocin and chlorhexidine or a pharmaceutically acceptable derivative thereof, for the prevention and/or treatment of microbial infections.

22 Claims, 15 Drawing Sheets

Figure 1 - Kill curve results for combination of 4-methyl-8-phenoxy-1-(2-phenylethyl)-2,3-dihydro-1H-pyrrolo[3,2-c]quinoline (4 µg/ml) with co-amoxiclav (* P < 0.0001)**
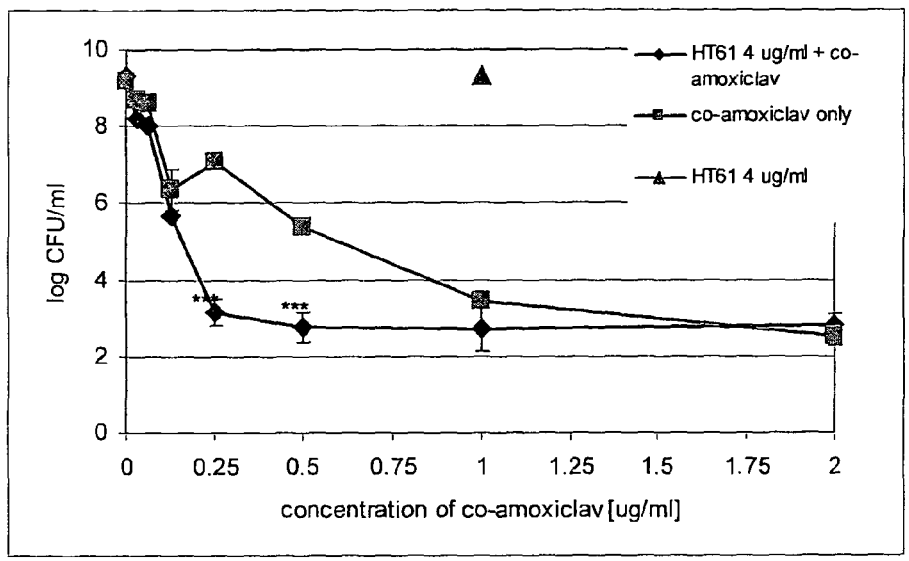
Figure 2 - 4-methyl-8-phenoxy-1-(2-phenylethyl)-2,3-dihydro-1H-pyrrolo[3,2-c]quinoline (10 µg/ml) in combination with mupirocin (40 µg/ml)
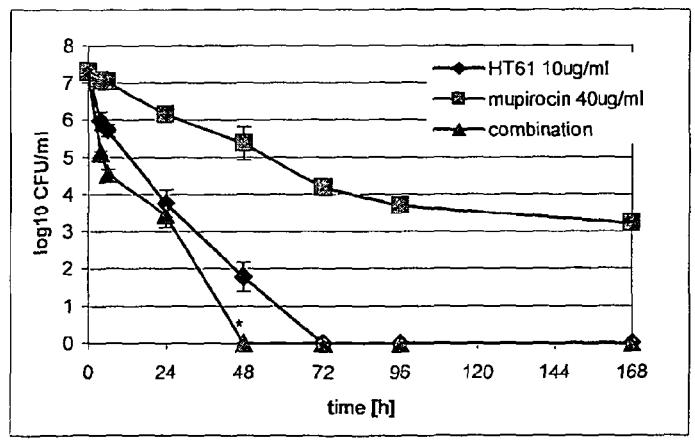

Figure 3 - 4-methyl-8-phenoxy-1-(2-phenylethyl)-2,3-dihydro-1H-pyrrolo[3,2-c]quinoline (10 μg/ml) in combination with mupirocin (20 μg/ml)
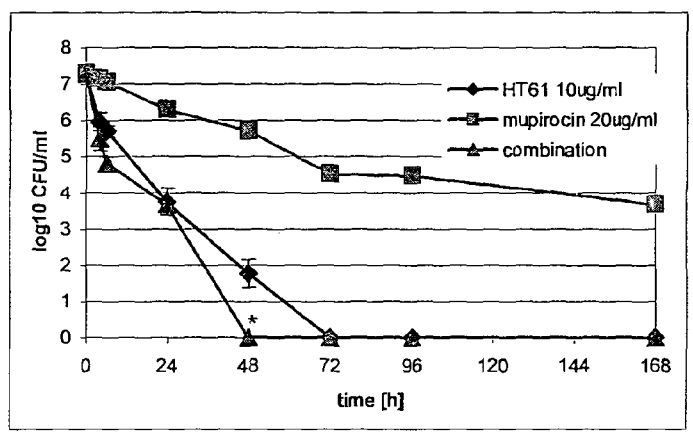
Figure 4 - 4-methyl-8-phenoxy-1-(2-phenylethyl)-2,3-dihydro-1H-pyrrolo[3,2-c]quinoline (10 μg/ml) in combination with mupirocin (10 μg/ml)
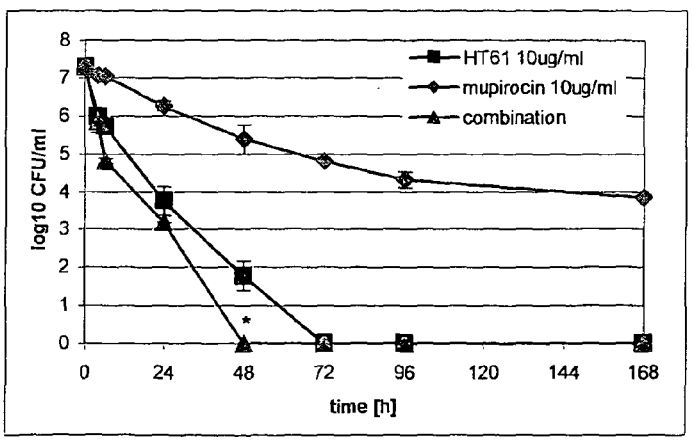

Figure 5 - 4-methyl-8-phenoxy-1-(2-phenylethyl)-2,3-dihydro-1H-pyrrolo[3,2-c]quinoline (8 µg/ml) in combination with mupirocin (40 µg/ml)
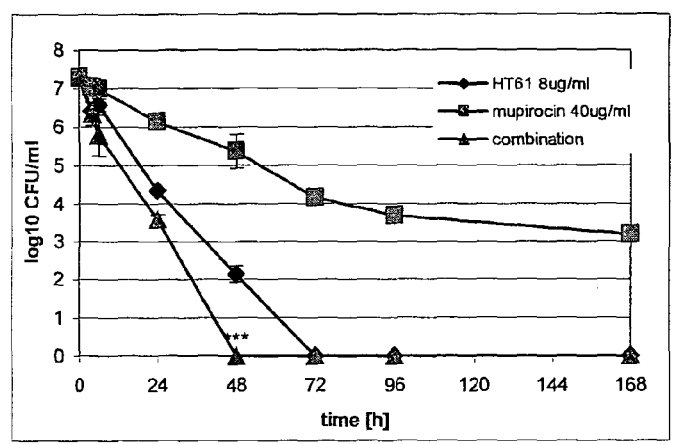
Figure 6 - 4-methyl-8-phenoxy-1-(2-phenylethyl)-2,3-dihydro-1H-pyrrolo[3,2-c]quinoline (8 µg/ml) in combination with mupirocin (20 µg/ml)
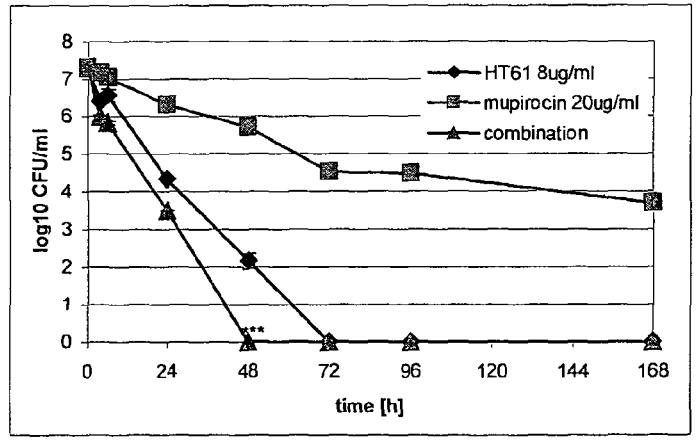

Figure 7 - 4-methyl-8-phenoxy-1-(2-phenylethyl)-2,3-dihydro-1H-pyrrolo[3,2-c]quinoline
(8 μg/ml) in combination with mupirocin (10 μg/ml)
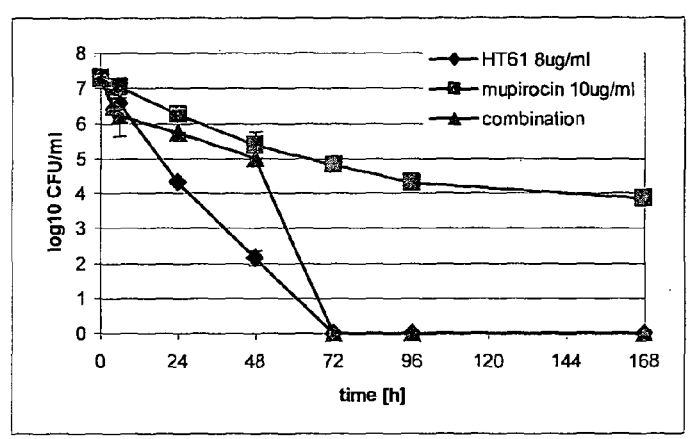
Figure 8 - 4-methyl-8-phenoxy-1-(2-phenylethyl)-2,3-dihydro-1H-pyrrolo[3,2-c]quinoline
(4 μg/ml) in combination with mupirocin (40 μg/ml)
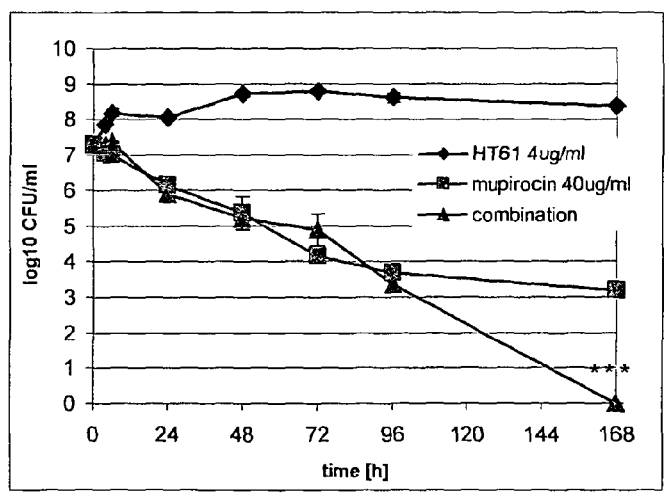

Figure 9 - 4-methyl-8-phenoxy-1-(2-phenylethyl)-2,3-dihydro-1H-pyrrolo[3,2-c]quinoline (4 µg/ml) in combination with mupirocin (20 µg/ml)
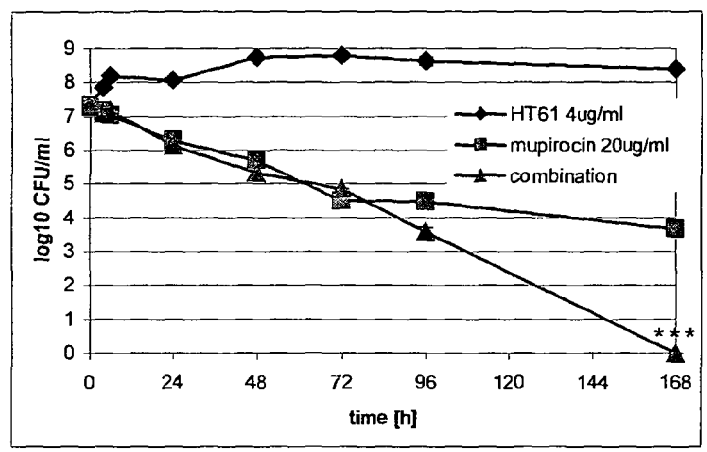
Figure 10 - 4-methyl-8-phenoxy-1-(2-phenylethyl)-2,3-dihydro-1H-pyrrolo[3,2-c]quinoline (4 µg/ml) in combination with mupirocin (10 µg/ml)
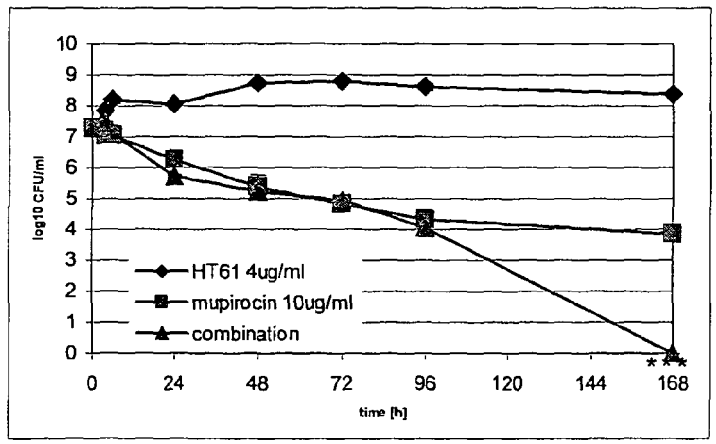

Figure 11 - Kill curve results for combination of 4-methyl-8-phenoxy-1-(2-phenylethyl)-2,3-dihydro-1H-pyrrolo[3,2-c]quinoline (5 µg/ml) with mupirocin

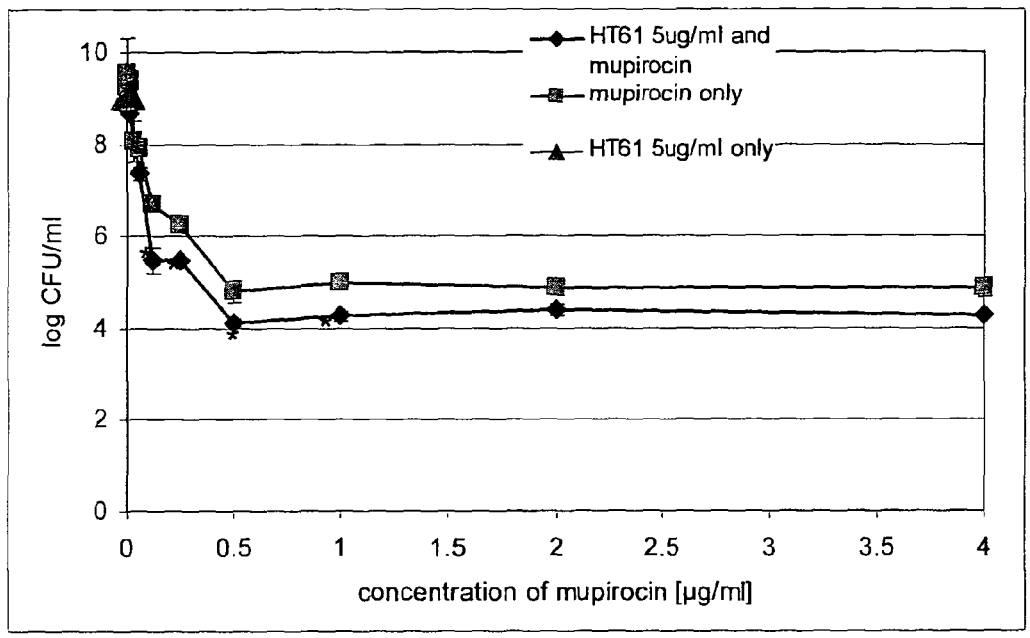

Figure 12 - Kill curve for 4-methyl-8-phenoxy-1-(2-phenylethyl)-2,3-dihydro-1H-pyrrolo[3,2-c]quinoline (5 µg/ml) in combination with chlorhexidine gluconate (against *S. Aureus* ($10^8$ inoculum)

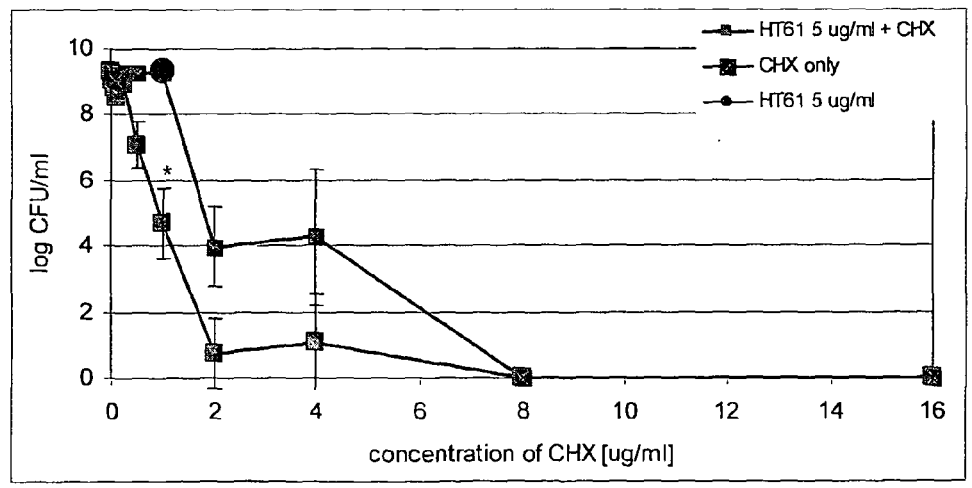

Results correspond to mean of viable bacteria ± standard deviation, * $P < 0.05$.

Figure 13 - Mean log CFU/ml ± standard deviations for a combination of 4-methyl-8-phenoxy-1-(2-phenylethyl)-2,3-dihydro-1H-pyrrolo[3,2-c]quinoline (4 µg/ml) with chlorhexidine gluconate (CHX) (0.5 and 1 µg/ml) and controls,  $P < 0.001$, * $P < 0.0001$ compared to 4-methyl-8-phenoxy-1-(2-phenylethyl)-2,3-dihydro-1H-pyrrolo[3,2-c]quinoline (4 µg/ml)
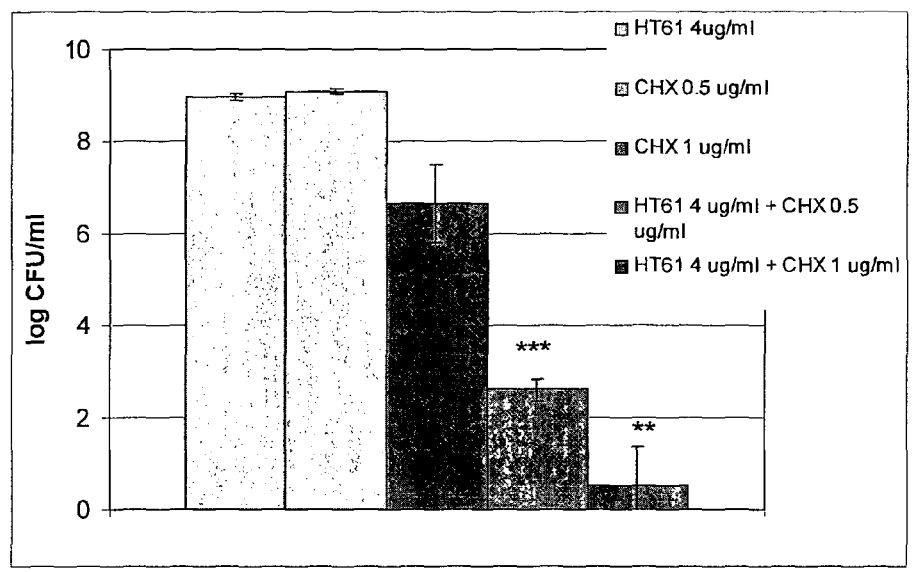

Figure 14 - Mean log CFU/ml ± standard deviations for a combination of 4-methyl-8-phenoxy-1-(2-phenylethyl)-2,3-dihydro-1H-pyrrolo[3,2-c]quinoline (5 μg/ml) with chlorhexidine gluconate (CHX) (0.5 and 1 μg/ml) and controls,  $P < 0.001$, * $P \le 0.0001$ compared to 4-methyl-8-phenoxy-1-(2-phenylethyl)-2,3-dihydro-1H-pyrrolo[3,2-c]quinoline (5 μg/ml)
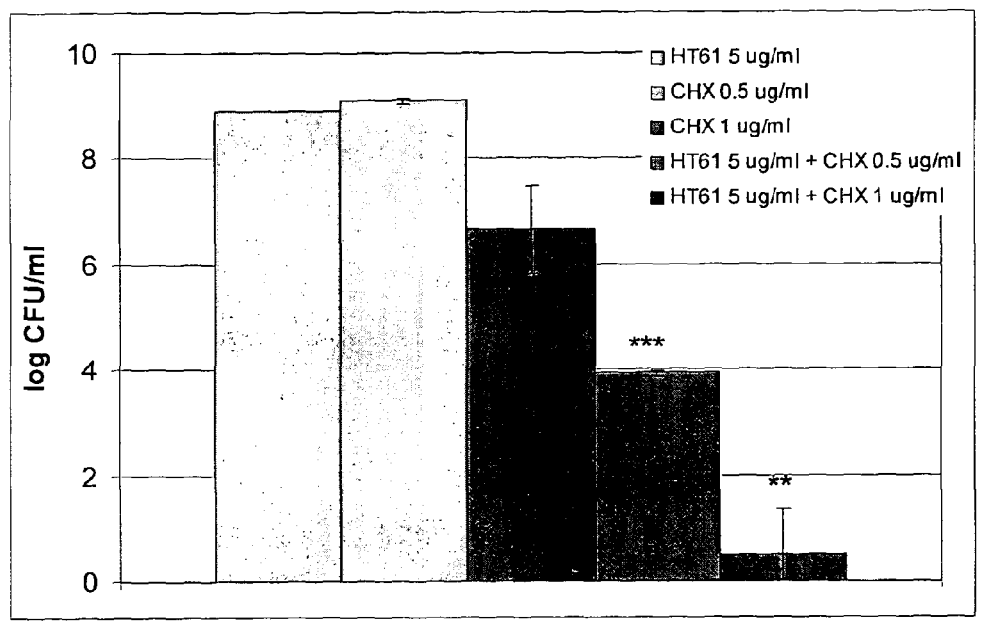

Figure 15 - 4-methyl-8-phenoxy-1-(2-phenylethyl)-2,3-dihydro-1H-pyrrolo[3,2-c]quinoline (8 μg/ml) in combination with chlorhexidine (8 μg/ml) against stationary phase MRSA
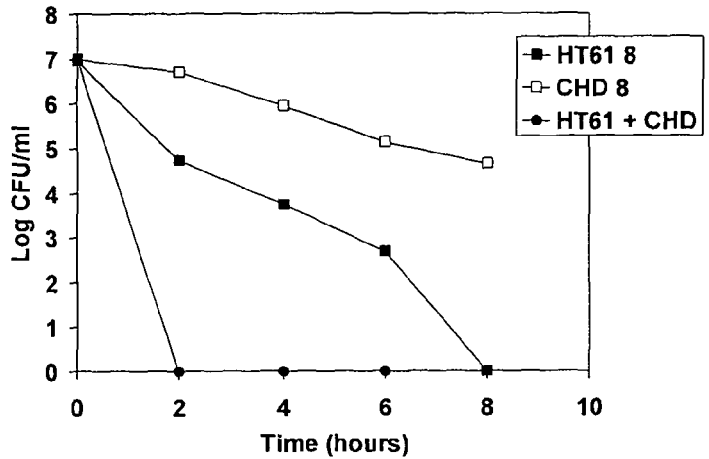
Figure 16 - 4-methyl-8-phenoxy-1-(2-phenylethyl)-2,3-dihydro-1H-pyrrolo[3,2-c]quinoline (8 μg/ml) in combination with chlorhexidine (4 μg/ml) against stationary phase MRSA
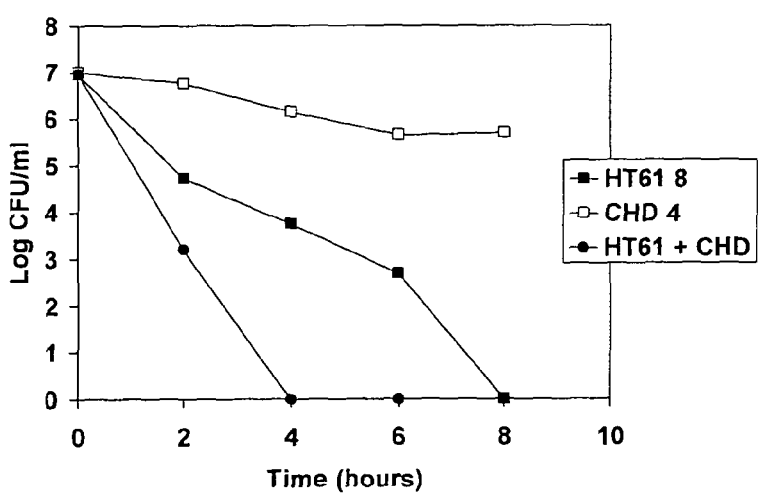

Figure 17 - 4-methyl-8-phenoxy-1-(2-phenylethyl)-2,3-dihydro-1H-pyrrolo[3,2-c]quinoline (8 µg/ml) in combination with chlorhexidine (2 µg/ml) against stationary phase MRSA
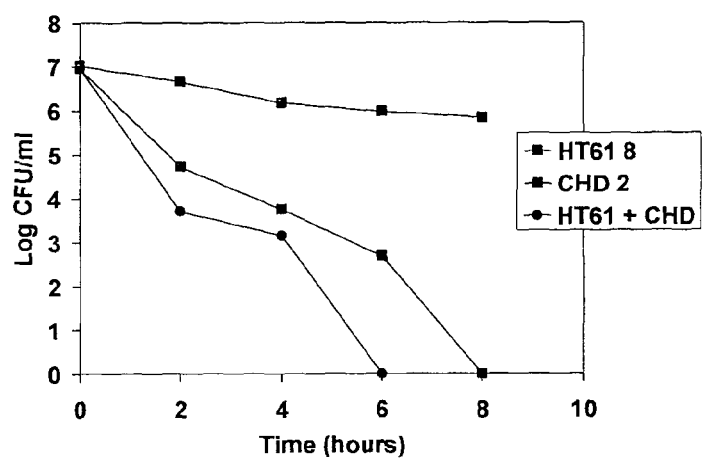
Figure 18 - 4-methyl-8-phenoxy-1-(2-phenylethyl)-2,3-dihydro-1H-pyrrolo[3,2-c]quinoline (4 µg/ml) in combination with chlorhexidine (8 µg/ml) against stationary phase MRSA
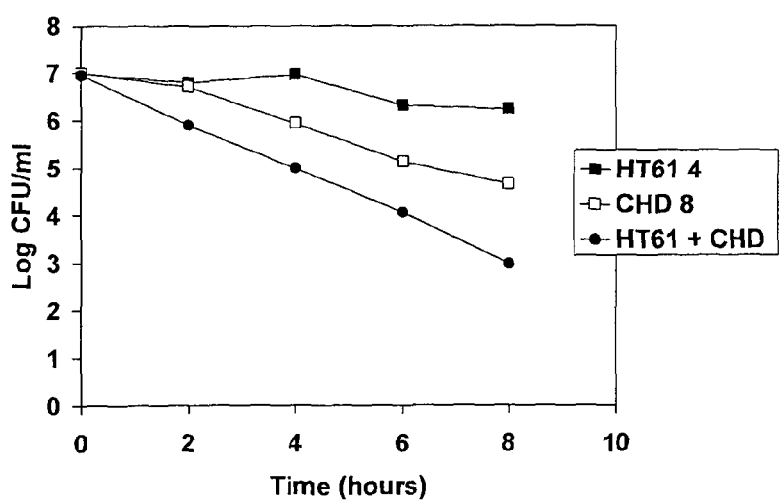

Figure 19 - 4-methyl-8-phenoxy-1-(2-phenylethyl)-2,3-dihydro-1H-pyrrolo[3,2-c]quinoline (4 µg/ml) in combination with chlorhexidine (4 µg/ml) against stationary phase MRSA
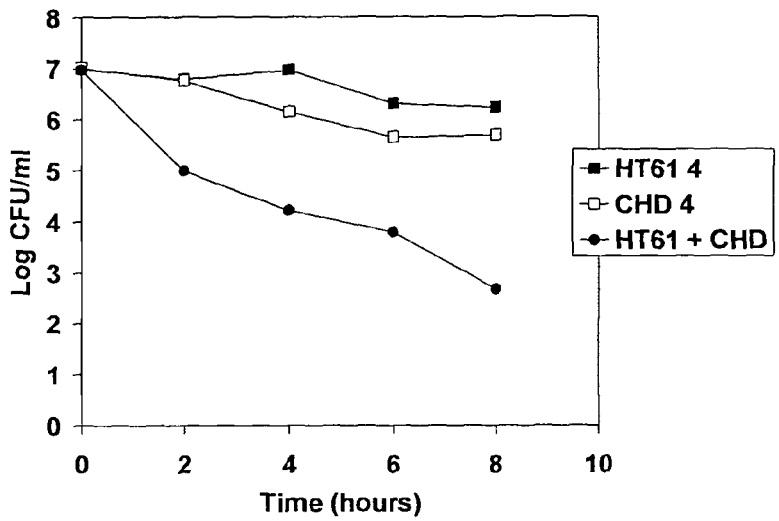
Figure 20 - 4-methyl-8-phenoxy-1-(2-phenylethyl)-2,3-dihydro-1H-pyrrolo[3,2-c]quinoline (2 µg/ml) in combination with chlorhexidine (4 µg/ml) against stationary phase MRSA
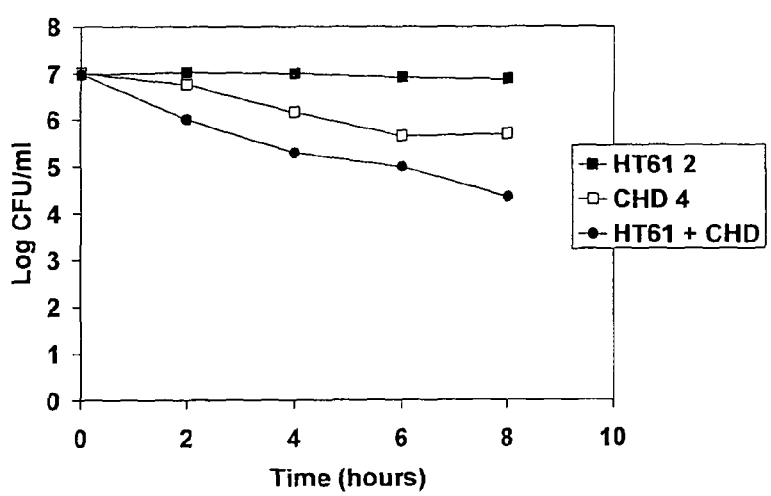

Figure 21 - 4-methyl-8-phenoxy-1-(2-phenylethyl)-2,3-dihydro-1H-pyrrolo[3,2-c]quinoline (4 µg/ml) in combination with chlorhexidine (8 µg/ml) against stationary phase MSSA
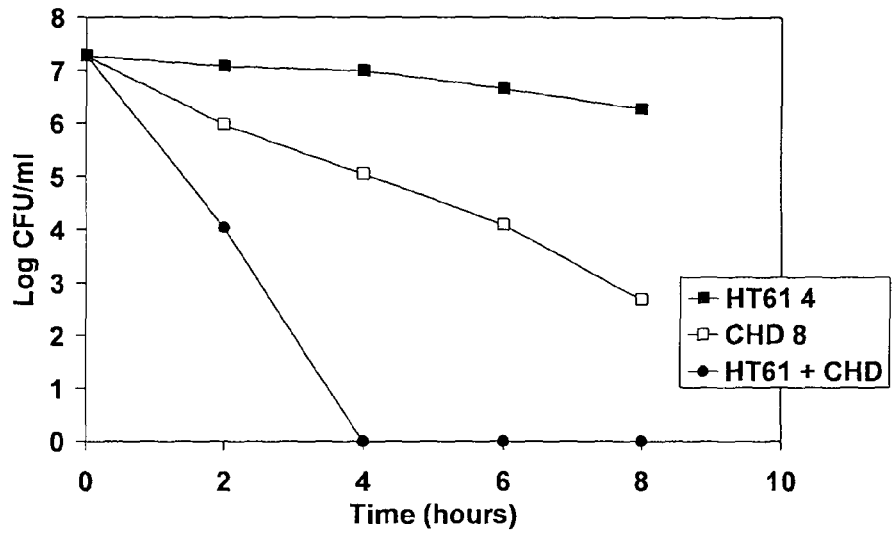
Figure 22 - 4-methyl-8-phenoxy-1-(2-phenylethyl)-2,3-dihydro-1H-pyrrolo[3,2-c]quinoline (4 µg/ml) in combination with chlorhexidine (4 µg/ml) against stationary phase MSSA
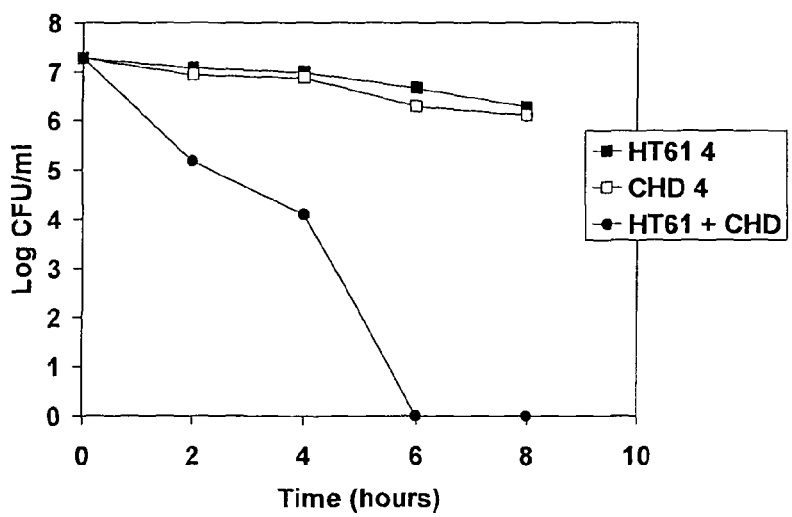

Figure 23 - 4-methyl-8-phenoxy-1-(2-phenylethyl)-2,3-dihydro-1H-pyrrolo[3,2-c]quinoline (4 µg/ml) in combination with chlorhexidine (2 µg/ml) against stationary phase MSSA
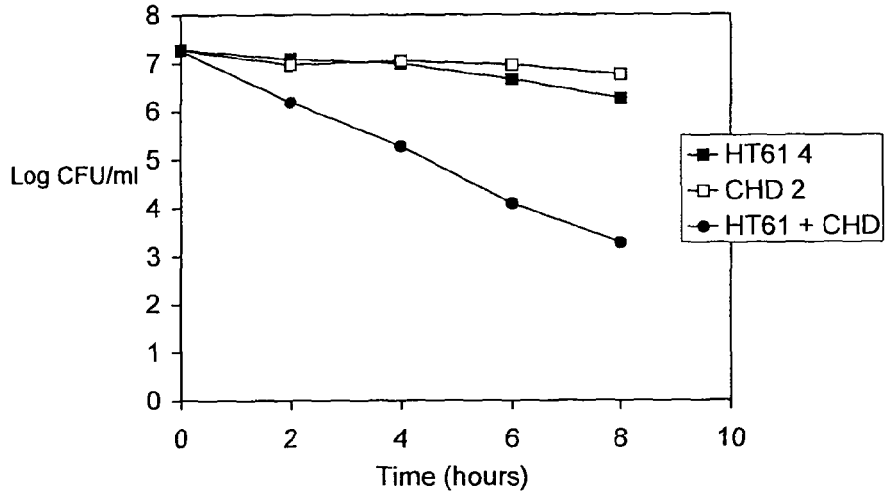
Figure 24 - 4-methyl-8-phenoxy-1-(2-phenylethyl)-2,3-dihydro-1H-pyrrolo[3,2-c]quinoline (2 µg/ml) in combination with chlorhexidine (8 µg/ml) against stationary phase MSSA
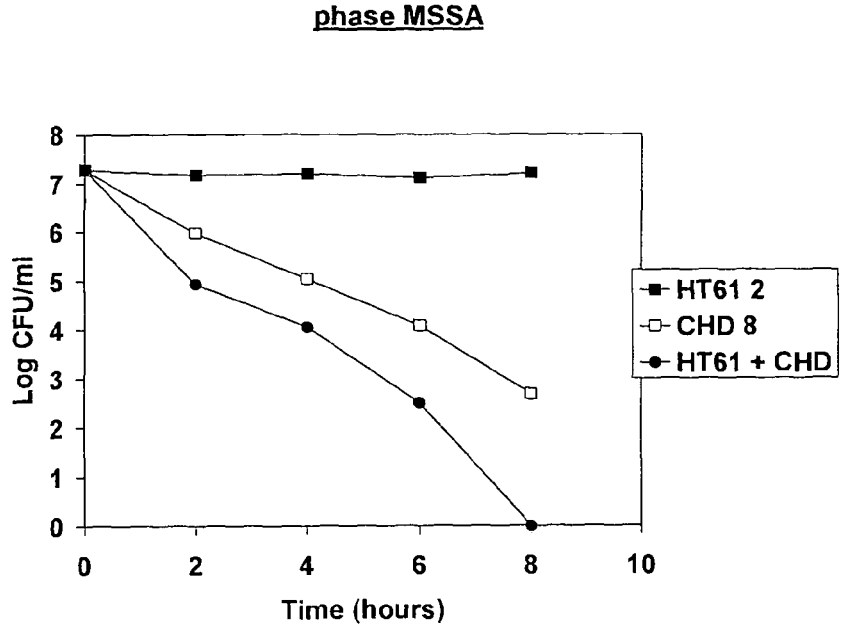

Figure 25 - 4-methyl-8-phenoxy-1-(2-phenylethyl)-2,3-dihydro-1H-pyrrolo[3,2-c]quinoline (2 μg/ml) in combination with chlorhexidine (4 μg/ml) against stationary phase MSSA
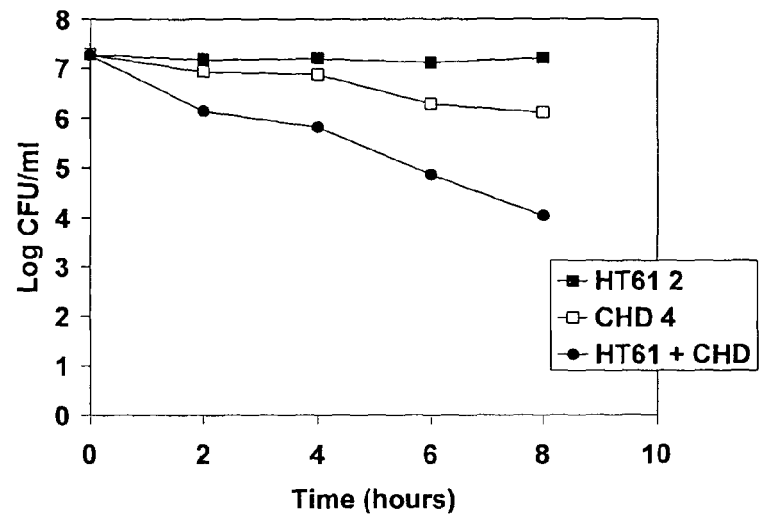
Figure 26 - 4-methyl-8-phenoxy-1-(2-phenylethyl)-2,3-dihydro-1H-pyrrolo[3,2-c]quinoline (2 μg/ml) in combination with chlorhexidine (4 μg/ml) against stationary phase MSSA
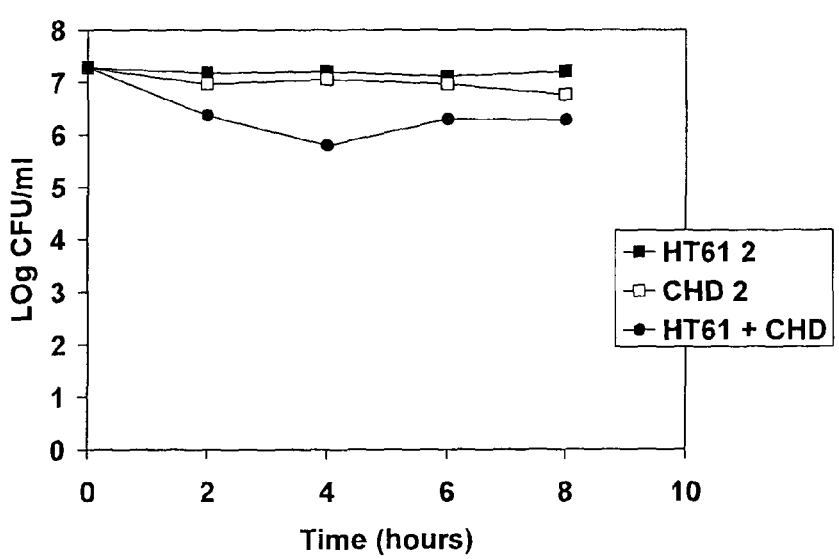

Figure 27 - 4-methyl-8-phenoxy-1-(2-phenylethyl)-2,3-dihydro-1H-pyrrolo[3,2-c]quinoline (8 µg/ml) in combination with chlorhexidine (8 µg/ml) against stationary phase MSSA
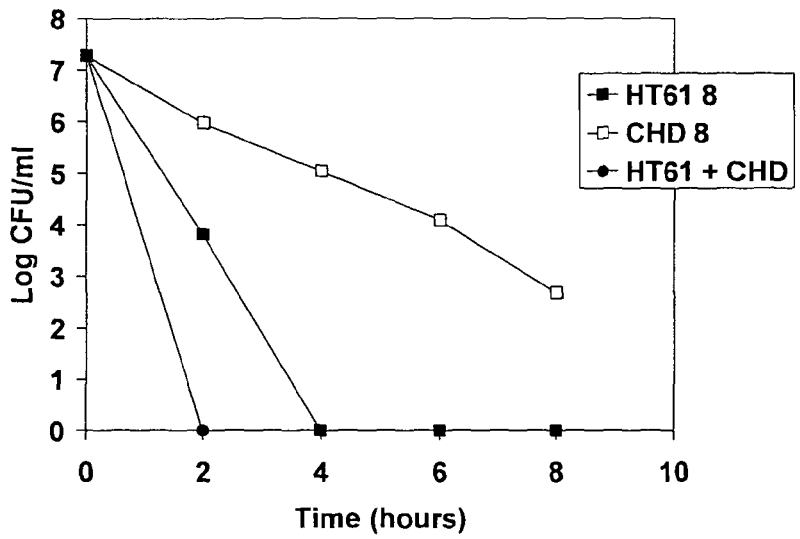
Figure 28 - 4-methyl-8-phenoxy-1-(2-phenylethyl)-2,3-dihydro-1H-pyrrolo[3,2-c]quinoline (8 µg/ml) in combination with chlorhexidine (4 µg/ml) against stationary phase MSSA
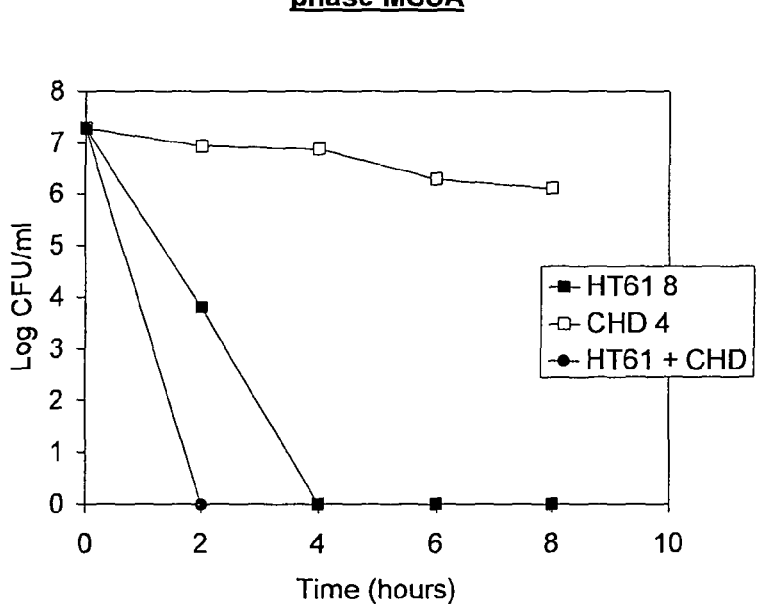

COMBINATION OF A PYRROLOQUINOLINE COMPOUND AND A BETA-LACTAM ANTIMICROBIAL AGENT, MUPIROCIN OR CHLORHEXIDINE

CLAIM FOR PRIORITY

This application claims priority under 35 USC 371 to International Application No. PCT/GB2011/001181, filed on Aug. 5, 2011, which claims priority to British Application No. 1013212.4, filed Aug. 5, 2010; British Application No. 1013209.0, filed Aug. 5, 2010; and British Application No. 1013214.0, filed Aug. 5, 2010, each of which is hereby incorporated by reference in its entirety.

This invention relates to a combination of antimicrobial agents for the prevention and/or treatment of microbial infections. In particular, it relates to the use of 4-methyl-8-phenoxy-1-(2-phenylethyl)-2,3-dihydro-1H-pyrrolo[3,2-c]quinoline or a pharmaceutically acceptable derivative thereof in combination with another antimicrobial agent selected from the group consisting of a beta-lactam antimicrobial agent, mupirocin and chlorhexidine or a pharmaceutically acceptable derivative thereof.

BACKGROUND

Before the introduction of antibiotics, patients suffering from acute microbial infections (e.g. tuberculosis or pneumonia) had a low chance of survival. For example, mortality from tuberculosis was around 50%. Although the introduction of antimicrobial agents in the 1940s and 1950s rapidly changed this picture, bacteria have responded by progressively gaining resistance to commonly used antibiotics. Now, every country in the world has antibiotic-resistant bacteria. Indeed, more than 70% of bacteria that give rise to hospital acquired infections in the USA resist at least one of the main antimicrobial agents that are typically used to fight infection (*Nature Reviews, Drug Discovery* 1, 895-910 (2002)).

One way of tackling the growing problem of resistant bacteria is the development of new classes of antimicrobial agents. However, until the introduction of linezolid in 2000, there had been no new class of antibiotic marketed for over 37 years. Moreover, even the development of new classes of antibiotic provides only a temporary solution, and indeed there are already reports of resistance of certain bacteria to linezolid (*Lancet* 357, 1179 (2001) and *Lancet* 358, 207-208 (2001)).

In order to develop more long-term solutions to the problem of bacterial resistance, it is clear that alternative approaches are required. One such alternative approach is to minimise, as much as is possible, the opportunities that bacteria are given for developing resistance to important antibiotics. Thus, strategies that can be adopted include limiting the use of antibiotics for the treatment of non-acute infections, as well as controlling which antibiotics are fed to animals in order to promote growth.

However, in order to tackle the problem more effectively, it is necessary to gain an understanding of the actual mechanisms by which bacteria generate resistance to antibiotic agents. To do this requires first a consideration of how current antibiotic agents work to kill bacteria.

Antimicrobial agents target essential components of bacterial metabolism. For example, the β-lactams (e.g. penicillins and cephalosporins) inhibit cell wall synthesis, whereas other agents inhibit a diverse range of targets, such as DNA gyrase (quinolones) and protein synthesis (e.g. macrolides, aminoglycosides, tetracyclines and oxazolidinones). The range of organisms against which the antimicrobial agents are effective varies, depending upon which organisms are heavily reliant upon the metabolic step(s) that is/are inhibited. Further, the effect upon bacteria can vary from a mere inhibition of growth (i.e. a bacteriostatic effect, as seen with agents such as the tetracyclines) to full killing (i.e. a bactericidal effect, as seen, e.g. with penicillin).

Bacteria have been growing on Earth for more than 3 billion years and, in that time, have needed to respond to vast numbers of environmental stresses. It is therefore perhaps not surprising that bacteria have developed a seemingly inexhaustible variety of mechanisms by which they can respond to the metabolic stresses imposed upon them by antibiotic agents. Indeed, mechanisms by which the bacteria can generate resistance include strategies as diverse as inactivation of the drug, modification of the site of action, modification of the permeability of the cell wall, overproduction of the target enzyme and bypass of the inhibited steps. Nevertheless, the rate of resistance emerges to a particular agent has been observed to vary widely, depending upon factors such as the agent's mechanism of action, whether the agent's mode of killing is time- or concentration-dependent, the potency against the population of bacteria and the magnitude and duration of the available serum concentration.

It has been proposed (*Science* 264, 388-393 (1994)) that agents that target single enzymes (e.g. rifampicin) are the most prone to the development of resistance. Further, the longer that suboptimal levels of antimicrobial agent are in contact with the bacteria, the more likely the emergence of resistance.

Moreover, it is now known that many microbial infections include sub-populations of bacteria that are phenotypically resistant to antimicrobials (*J. Antimicrob. Chemother.* 4, 395-404 (1988); *J. Med. Microbial.* 38, 197-202 (1993); *J. Bacteria* 182, 1794-1801 (2000); *ibid.* 182, 6358-6365 (2000); *ibid.* 183, 6746-6751 (2001); *FEMS Microbiol, Lett.* 202, 59-65 (2001); and *Trends in Microbiology* 13, 34-40 (2005)). There appear to be several types of such phenotypically resistant bacteria, including persisters, stationary-phase bacteria, as well as those in the depths of biofilms. However, each of these types is characterised by its low rate of growth compared to log-phase bacteria under the same conditions. Nutritional starvation and high cell densities are also common characteristics of such bacteria.

Although resistant to antimicrobial agents in their slow-growing state, phenotypically resistant bacteria differ from those that are genotypically resistant in that they regain their susceptibility to antimicrobials when they return to a fast-growing state (e.g. when nutrients become more readily available to them).

The presence of phenotypically resistant bacteria in an infection leads to the need for prolonged courses of antimicrobial agents, comprising multiple doses. This is because the resistant, slowly multiplying bacteria provide a pool of "latent" organisms that can convert to a fast-growing state when the conditions allow (thereby effectively re-initiating the infection). Multiple doses over time deal with this issue by gradually killing off the "latent" bacteria that convert to "active" form.

However, dealing with "latent" bacteria by administering prolonged courses of antimicrobials poses its own problems. That is, prolonged exposure of bacteria to suboptimal concentrations of antimicrobial agent can lead to the emergence of genotypically resistant bacteria, which can then multiply rapidly in the presence of even high concentrations of the antimicrobial.

Long courses of antimicrobials are more likely to encourage the emergence of genotypic resistance than shorter courses on the grounds that non-multiplying bacterial will tend to survive and, interestingly, probably have an enhanced ability to mutate to resistance (*Proc. Natl. Acad. Sci. USA* 92, 11736-11740 (1995); *J. Bacteriol.* 179, 6688-6691 (1997); and *Antimicrob. Agents Chemother.* 44, 1771-1777 (2000)).

In the light of the above, a new approach to combating the problem of bacterial resistance might be to select and develop antimicrobial agents on the basis of their ability to kill "latent" microorganisms. The production of such agents would allow, amongst other things, for the shortening of chemotherapy regimes in the treatment of microbial infections, thus reducing the frequency with which genotypical resistance arises in microorganisms.

International Patent Application, Publication Number WO2000028074 describes a method of screening compounds to determine their ability to kill clinically latent microorganisms. Using this method, the Applicant has observed that many conventional antimicrobial agents, such as co-amoxiclav, azithromycin, levofloxacin, linezolid and mupirocin, which otherwise exhibit excellent biological activity against log phase (i.e. multiplying) bacteria, exhibit little or no activity against clinically latent microorganisms. This observation has necessitated the development of novel antimicrobials which may be used to kill clinically latent microorganisms.

International Patent Application, Publication Numbers WO2007054693, WO2008117079 and WO2008142384 describe compounds which exhibit biological activity against clinically latent microorganisms. Examples of such compounds include 4-methyl-8-phenoxy-1-(2-phenylethyl)-2,3-dihydro-1H-pyrrolo[3,2-c]quinoline, 4-(3-benzylpyrrolidin-1-yl)-2-methyl-6-phenoxyquinoline, N-[4-(3-benzylpyrrolidin-1-yl)-2-methylquinolin-6-yl]benzamide and pharmaceutically acceptable derivatives thereof.

Co-amoxiclav is a fixed dose combination product which consists of amoxicillin (in trihydrate form) and clavulanic acid (in the form of potassium clavulanate).

SUMMARY

Amoxicillin is a semi-synthetic derivative of penicillin which belongs to the class of beta-lactam antibiotics. It acts by inhibiting one or more enzymes in the biosynthetic pathway of bacterial peptidoglycan, which is an integral component of the bacterial cell wall. Inhibition of peptidoglycan synthesis leads to weakening of the cell wall, which is usually followed by cell lysis and death.

Clavulanic acid is a beta-lactam that is structurally related to penicillin. It inactivates some beta-lactamase enzymes thereby preventing inactivation of amoxicillin. Clavulanic acid alone does not exhibit a clinically useful antibacterial effect.

Co-amoxiclav is commercially available in Europe under the trade name Augmentin® in tablet, suspension and intravenous forms. Augmentin® is indicated for the treatment of a number of bacterial infections including acute bacterial sinusitis, acute otitis media, cystitis and skin and soft tissue infections.

Mupirocin is an antibiotic originally isolated from *Pseudomonas fluorescens*. Mupirocin acts as a potent inhibitor of bacterial protein and RNA synthesis by inhibition of isoleucyl-transfer RNA synthase. It is known to be effective against a wide variety of bacteria including *Staphylococcus aureus*, including methicillin-resistant strains, and Gram-negative organisms such as *Escherichia coli* and *Haemophilus influenzae*. Mupirocin is commercially available in Europe under the trade name Bactroban® in cream and ointment form. Bactroban® is indicated for the treatment of skin infections such as impetigo, folliculitis and furunculosis. It is also indicated for the eradication of *S. aureus* from the anterior nares, where it is located in about 20% of people and decolonisation of the nose for MRSA. Removal of *S. aureus* from the nose in hospital inpatients is associated with a decrease in the incidence of surgical site (Bode et al., *N. Engl. J. Med.*, 362(1), 9-17, (2010)) and nosocomial (Perl et al., *N. Engl. J. Med.*, 346(24), 1871-1877, (2002)) infections.

The antibacterial activity of mupirocin in combination with certain other antibiotics has been reported previously. For example, Ghiselli et al. (*J. Surg. Res.*, 99(2), 316-320, (2001)) have studied the effect of mupirocin in combination with amoxicillin-clavulate, which produced complete suppression of growth of *S. aureus* and MRSA in a rat model of the prevention of vascular prosthetic graft infections. In addition, Alou et al. (*J. Antimicrob. Agents*, 23(5), 513-516, (2004)) observed a 2.5 $\log_{10}$ CFU/ml reduction for a $10^6$ CFU/ml inoculum of *S. aureus* for a combination of mupirocin and amoxicillin-clavulate.

Chlorhexidine is a commercially available antiseptic compound. It is sold in Europe under a variety of trade names for various therapeutic indications. For example, Corsodyl® is a mouthwash comprising chlorhexidine digluconate (0.2% w/v) which is indicated for the inhibition of the formation of dental plaque, as an aid in the treatment and prevention of gingivitis, and in the maintenance of oral hygiene.

The present invention is based upon the unexpected finding that the antimicrobial activity of certain antimicrobial agents, in particular mupirocin and chlorhexidine, and beta-lactam antimicrobial agents such as co-amoxiclav, is substantially improved when these agents are administered in combination with the compound 4-methyl-8-phenoxy-1-(2-phenylethyl)-2,3-dihydro-1H-pyrrolo[3,2-c]quinoline or a pharmaceutically acceptable derivative thereof. Moreover, certain of these combinations of active agents have surprisingly been shown to exhibit synergistic antimicrobial activity against log phase (i.e. multiplying) and stationary phase (i.e. non-multiplying) microorganisms. The surprising biological activity of the combinations of the present invention offers the opportunity to shorten chemotherapy regimes and may result in a reduction in the emergence of microbial resistance associated with the use of such combinations.

Thus, in one embodiment the present invention provides 4-methyl-8-phenoxy-1-(2-phenylethyl)-2,3-dihydro-1H-pyrrolo[3,2-c]quinoline or a pharmaceutically acceptable derivative thereof and another antimicrobial agent selected from the group consisting of a beta-lactam antimicrobial agent, mupirocin and chlorhexidine or a pharmaceutically acceptable derivative thereof.

In a further embodiment, the present invention provides a combination comprising 4-methyl-8-phenoxy-1-(2-phenylethyl)-2,3-dihydro-1H-pyrrolo[3,2-c]quinoline or a pharmaceutically acceptable derivative thereof and another antimicrobial agent selected from the group consisting of a beta-lactam antimicrobial agent, mupirocin and chlorhexidine or a pharmaceutically acceptable derivative thereof.

In another embodiment, the present invention provides the use of 4-methyl-8-phenoxy-1-(2-phenylethyl)-2,3-dihydro-1H-pyrrolo[3,2-c]quinoline or a pharmaceutically acceptable derivative thereof in combination with another antimicrobial agent selected from the group consisting of a beta-lactam antimicrobial agent, mupirocin and chlorhexidine or a pharmaceutically acceptable derivative thereof for the manufacture of a medicament for the prevention and/or treatment of a microbial infection; in particular for killing multiplying, non-multiplying and/or clinically latent microorganisms associated with such an infection.

BRIEF DESCRIPTION OF THE DRAWINGS

FIGS. 1-28 represent kill curve results.

DETAILED DESCRIPTION

The invention further provides a method of preventing or treating a microbial infection, in particular killing multiplying, non-multiplying and/or clinically latent microorganisms associated with such an infection, which comprises administering to a mammal, including man, 4-methyl-8-phenoxy-1-(2-phenylethyl)-2,3-dihydro-1H-pyrrolo[3,2-c]quinoline or a pharmaceutically acceptable derivative thereof in combination with another antimicrobial agent selected from the group consisting of a beta-lactam antimicrobial agent, mupirocin and chlorhexidine or a pharmaceutically acceptable derivative thereof.

In another embodiment, the invention provides the use of 4-methyl-8-phenoxy-1-(2-phenylethyl)-2,3-dihydro-1H-pyrrolo[3,2-c]quinoline or a pharmaceutically acceptable derivative thereof in combination with another antimicrobial agent selected from the group consisting of a beta-lactam antimicrobial agent, mupirocin and chlorhexidine or a pharmaceutically acceptable derivative thereof for the prevention and/or treatment of a microbial infection; in particular for killing multiplying, non-multiplying and/or clinically latent microorganisms associated with such an infection.

As used herein, the terms "combination" and "in combination with" refer to both separate and sequential administration of 4-methyl-8-phenoxy-1-(2-phenylethyl)-2,3-dihydro-1H-pyrrolo[3,2-c]quinoline or a pharmaceutically acceptable derivative thereof and a beta-lactam antimicrobial agent, mupirocin or chlorhexidine or a pharmaceutically acceptable derivative thereof. When the agents are administered sequentially, either 4-methyl-8-phenoxy-1-(2-phenylethyl)-2,3-dihydro-1H-pyrrolo[3,2-c]quinoline or a pharmaceutically acceptable derivative thereof, or a beta-lactam antimicrobial agent, mupirocin or chlorhexidine or a pharmaceutically acceptable derivative thereof may be administered first. When administration is simultaneous, the agents may be administered either in the same or a different pharmaceutical composition. Adjunctive therapy, i.e. where one agent is used as a primary treatment and the other agent is used to assist that primary treatment, is also an embodiment of the present invention.

According to a further embodiment of the invention, there is provided a product comprising 4-methyl-8-phenoxy-1-(2-phenylethyl)-2,3-dihydro-1H-pyrrolo[3,2-c]quinoline or a pharmaceutically acceptable derivative thereof and another antimicrobial agent selected from the group consisting of a beta-lactam antimicrobial agent, mupirocin and chlorhexidine or a pharmaceutically acceptable derivative thereof as a combined preparation for simultaneous, separate or sequential use in the prevention and/or treatment of a microbial infection.

There is also provided a pharmaceutical composition comprising 4-methyl-8-phenoxy-1-(2-phenylethyl)-2,3-dihydro-1H-pyrrolo[3,2-c]quinoline or a pharmaceutically acceptable derivative thereof, another antimicrobial agent selected from the group consisting of a beta-lactam antimicrobial agent, mupirocin and chlorhexidine or a pharmaceutically acceptable derivative thereof, and a pharmaceutically acceptable adjuvant, diluent or carrier. Such a composition may be used for the prevention and/or treatment of microbial infections, and in particular for use in killing multiplying, non-multiplying and/or clinically latent microorganisms associated with a microbial infection.

The combinations of the present invention may be used to prevent and/or treat microbial infections. In particular they may be used to kill multiplying, non-multiplying and/or clinically latent microorganisms associated with microbial infections. References herein to the treatment of a microbial infection therefore include killing multiplying, non-multiplying and/or clinically latent microorganisms associated with such infections.

In one embodiment of the invention, there is provided a combination comprising 4-methyl-8-phenoxy-1-(2-phenylethyl)-2,3-dihydro-1H-pyrrolo[3,2-c]quinoline or a pharmaceutically acceptable and a beta lactam antimicrobial agent. Suitable beta-lactams for use in the present invention include the following compounds:

(i) penicillins, such as
  (I) benzylpenicillin, procaine benzylpenicillin, phenoxy-methylpenicillin, methicillin, propicillin, epicillin, cyclacillin, hetacillin, 6-aminopenicillanic acid, penicillic acid, penicillanic acid sulphone (sulbactam), penicillin G, penicillin V, phenethicillin, phenoxymethylpenicillinic acid, azlocillin, carbenicillin, cloxacillin, D-(−)-penicillamine, dicloxacillin, nafcillin and oxacillin,
  (II) penicillinase-resistant penicillins (e.g. flucloxacillin),
  (III) broad-spectrum penicillins (e.g. ampicillin, amoxicillin, metampicillin and bacampicillin),
  (IV) antipseudomonal penicillins (e.g. carboxypenicillins such as ticarcillin or ureidopenicillins such as piperacillin),
  (V) mecillinams (e.g. pivmecillinam), or
  (VI) combinations of any two or more of the agents mentioned at (I) to (V) above, or combinations of any of the agents mentioned at (I) to (V) above with a β-lactamase inhibitor such as tazobactam or, particularly, clavulanic acid (which acid is optionally in metal salt form, e.g. in salt form with an alkali metal such as sodium or, particularly, potassium);
(ii) cephalosporins, such as cefaclor, cefadroxil, cefalexin (cephalexin), cefcapene, cefcapene pivoxil, cefdinir, cefditoren, cefditoren pivoxil, cefixime, cefotaxime, cefpirome, cefpodoxime, cefpodoxime proxetil, cefprozil, cefradine, ceftazidime, cefteram, cefteram pivoxii, ceftriaxone, cefuroxime, cefuroxime axetil, cephaloridine, cephacetrile, cephamandole, cephaloglycine, ceftobiprole, PPI-0903 (TAK-599), 7-aminocephalosporanic acid, 7-aminodes-acetoxycephalosporanic acid, cefamandole, cefazolin, cefmetazole, cefoperazone, cefsulodin, cephalosporin C zinc salt, cephalothin, cephapirin; and
(iii) other β-lactams, such as monobactams (e.g. aztreonam), carbapenems (e.g. imipenem (optionally in combination with a renal enzyme inhibitor such as cilastatin), meropenem, ertapenem, doripenem (S-4661) and RO4908463 (CS-023)), penems (e.g. faropenem) and 1-oxa-β-lactams (e.g. moxalactam).

In one embodiment of the invention, the beta-lactam is penicillin or a derivative thereof. In an alternative embodiment of the invention, the beta-lactam is a cephalosporin. A particularly preferred beta-lactam is co-amoxiclav.

In an alternative embodiment of the invention, there is provided a combination comprising 4-methyl-8-phenoxy-1-

(2-phenylethyl)-2,3-dihydro-1H-pyrrolo[3,2-c]quinoline or a pharmaceutically acceptable derivative thereof and mupirocin.

In a further alternative embodiment of the invention, there is provided a combination comprising 4-methyl-8-phenoxy-1-(2-phenylethyl)-2,3-dihydro-1H-pyrrolo[3,2-c]quinoline or a pharmaceutically acceptable derivative thereof and chlorhexidine.

As used herein, "kill" means a loss of viability as assessed by a lack of metabolic activity.

As used herein, "clinically latent microorganism" means a microorganism that is metabolically active but has a growth rate that is below the threshold of infectious disease expression. The threshold of infectious disease expression refers to the growth rate threshold below which symptoms of infectious disease in a host are absent.

The metabolic activity of clinically latent microorganisms can be determined by several methods known to those skilled in the art; for example, by measuring mRNA levels in the microorganisms or by determining their rate of uridine uptake. In this respect, clinically latent microorganisms, when compared to microorganisms under logarithmic growth conditions (in vitro or in vivo), possess reduced but still significant levels of:

(I) mRNA (e.g. from 0.0001 to 50%, such as from 1 to 30, 5 to 25 or 10 to 20%, of the level of mRNA); and/or (II) uridine (e.g. [$^3$H]uridine) uptake (e.g. from 0.0005 to 50%, such as from 1 to 40, 15 to 35 or 20 to 30% of the level of [$^3$H]uridine uptake).

Clinically latent microorganisms typically possess a number of identifiable characteristics. For example, they may be viable but non-culturable; i.e. they cannot typically be detected by standard culture techniques, but are detectable and quantifiable by techniques such as broth dilution counting, microscopy, or molecular techniques such as polymerase chain reaction. In addition, clinically latent microorganisms are phenotypically tolerant, and as such are sensitive (in log phase) to the biostatic effects of conventional antimicrobial agents (i.e. microorganisms for which the minimum inhibitory concentration (MIC) of a conventional antimicrobial is substantially unchanged); but possess drastically decreased susceptibility to drug-induced killing (e.g. microorganisms for which, with any given conventional antimicrobial agent, the ratio of minimum microbiocidal concentration (e.g. minimum bactericidal concentration, MBC) to MIC is 10 or more).

As used herein, the term "microorganisms" means fungi and bacteria. References herein to "microbial", "antimicrobial" and "antimicrobially" shall be interpreted accordingly. For example, the term "microbial" means fungal or bacterial, and "microbial infection" means any fungal or bacterial infection.

As used herein, the term "bacteria" (and derivatives thereof, such as "microbial infection") includes, but is not limited to, references to organisms (or infections due to organisms) of the following classes and specific types:

Gram-positive cocci, such as Staphylococci (e.g. *Staph. aureus, Staph. epidermidis, Staph. saprophyticus, Staph. auricularis, Staph. capitis capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pasteuri, Staph. saccharolyticus, Staph. schleiferi schleiferi, Staph. s. coagulans, Staph. sciuri, Staph. simulans, Staph. warned* and *Staph. xylosus*);

Streptococci (e.g. beta-haemolytic, pyogenic *streptococci* (such as *Strept. agalactiae, Strept. canis, Strept dysgalactiae dysgalactiae, Strept dysgalactiae equisimilis, Strept equi equi, Strept. equi zooepidemicus, Strept. iniae, Strept porcinus* and *Strept pyogenes*), microaerophilic, pyogenic *streptococci* (*Streptococcus "milleri"*, such as *Strept. anginosus, Strept constellatus constellatus, Strept constellatus pharyngidis* and *Strept intermedius*), oral *streptococci* of the "mitis" (alpha-haemolytic—*Streptococcus "viridans"*, such as *Strept. mitis, Strept. ovalis, Strept. sanguinis, Strept. cristatus, Strept gordonii* and *Strept. parasanguinis*), "salivarius" (non-haemolytic, such as *Strept salivarius* and *Strept. vestibularis*) and "mutans" (tooth-surface *streptococci*, such as *Strept. criceti, Strept. mutans, Strept ratti* and *Strept sobrinus*) groups, *Strept acidominimus, Strept. bovis, Strept faecalis, Strept. equinus, Strept. pneumoniae* and *Strept. suis*, or *Streptococci* alternatively classified as Group A, B, C, D, E, G, L, P, U or V *Streptococcus*);

Gram-negative cocci, such as *Neisseria gonorrhoeae, Neisseria meningitidis, Neisseria cinerea, Neisseria elongata, Neisseria flavescens, Neisseria lactamica, Neisseria mucosa, Neisseria sicca, Neisseria subflava* and *Neisseria weaveri*;

Bacillaceae, such as *Bacillus anthracis, Bacillus subtilis, Bacillus thuringiensis, Bacillus stearothermophilus* and *Bacillus cereus*;

Enterobacteriaceae, such as *Escherichia coli, Enterobacter* (e.g. *Enterobacter aerogenes, Enterobacter agglomerans* and *Enterobacter cloacae*), *Citrobacter* (such as *Citrob. freundii* and *Citrob. divernis*), *Hafnia* (e.g. *Hafnia alvei*), *Erwinia* (e.g. *Erwinia persicinus*), *Morganella morganii, Salmonella* (*Salmonella enterica* and *Salmonella typhi*), *Shigella* (e.g. *Shigella dysenteriae, Shigella flexneri, Shigella boydii* and *Shigella sonnei*), *Klebsiella* (e.g. *Klebs. pneumoniae, Klebs. oxytoca, Klebs. ornitholytica, Klebs. planticola, Klebs. ozaenae, Klebs. terrigena, Klebs. granulomatis* (*Calymmatobacterium granulomatis*) and *Klebs. rhinoscleromatis*), *Proteus* (e.g. *Pr. mirabilis, Pr. rettgeri* and *Pr. vulgaris*), *Providencia* (e.g. *Providencia alcalifaciens, Providencia rettgeri* and *Providencia stuartii*), *Serratia* (e.g. *Serratia marcescens* and *Serratia liquifaciens*), and *Yersinia* (e.g. *Yersinia enterocolitica, Yersinia pestis* and *Yersinia pseudotuberculosis*);

Enterococci (e.g. *Enterococcus avium, Enterococcus casseliflavus, Enterococcus cecorum, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus* and *Enterococcus solitarius*);

Helicobacter (e.g. *Helicobacter pylori, Helicobacter cinaedi* and *Helicobacter fennelliae*);

Acinetobacter (e.g. *A. baumanii, A. calcoaceticus, A. haemolyticus, A. johnsonii, A. junii, A. lwoffi* and *A. radioresistens*);

Pseudomonas (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzen*);

Bacteriodes fragilis;

Peptococcus (e.g. *Peptococcus niger*);

Peptostreptococcus;

Clostridium (e.g. *C. perfringens, C. difficile, C. botulinum, C. tetani, C. absonum, C. argentinense, C. baratii, C. bifermentans, C. beijerinckii, C. butyricum, C. cadaveris, C. camis, C. celatum, C. clostridioforme, C. cochlearium, C. cocleatum, C. fallax, C. ghonii, C. glycolicum, C. haemolyti-*

*cum, C. hastiforme, C. histolyticum, C. indolis, C. innocuum, C. irregulare, C. leptum, C. limosum, C. malenominatum, C. novyi, C. oroticum, C. paraputrificum, C. piliforme, C. putrefasciens, C. ramosum, C. septicum, C. sordelii, C. sphenoides, C. sporogenes, C. subterminale, C. symbiosum* and *C. tedium*);

Mycoplasma (e.g. *M. pneumoniae, M. hominis, M. genitalium* and *M. urealyticum*);

Mycobacteria (e.g. *Mycobacterium tuberculosis, Mycobacterium avium, Mycobacterium fortuitum, Mycobacterium marinum, Mycobacterium kansasii, Mycobacterium chelonae, Mycobacterium abscessus, Mycobacterium leprae, Mycobacterium smegmitis, Mycobacterium africanum, Mycobacterium alvei, Mycobacterium asiaticum, Mycobacterium aurum, Mycobacterium bohemicum, Mycobacterium bovis, Mycobacterium branderi, Mycobacterium brumae, Mycobacterium celatum, Mycobacterium chubense, Mycobacterium confluentis, Mycobacterium conspicuum, Mycobacterium cookii, Mycobacterium flavescens, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium lentiflavum, Mycobacterium malmoense, Mycobacterium microgenicum, Mycobacterium microti, Mycobacterium mucogenicum, Mycobacterium neoaurum, Mycobacterium nonchromogenicum, Mycobacterium peregrinum, Mycobacterium phlei, Mycobacterium scrofulaceum, Mycobacterium shimoidei, Mycobacterium simiae, Mycobacterium szulgai, Mycobacterium terrae, Mycobacterium thermoresistabile, Mycobacterium triplex, Mycobacterium triviale, Mycobacterium tusciae, Mycobacterium ulcerans, Mycobacterium vaccae, Mycobacterium wolinskyi* and *Mycobacterium xenopi*);

Haemophilus (e.g. *Haemophilus influenzae, Haemophilus ducreyi, Haemophilus aegyptius, Haemophilus parainfluenzae, Haemophilus haemolyticus* and *Haemophilus parahaemolyticus*);

Actinobacillus (e.g. *Actinobacillus actinomycetemcomitans, Actinobacillus equuli, Actinobacillus hominis, Actinobacillus lignieresii, Actinobacillus suis* and *Actinobacillus ureae*);

Actinomyces (e.g. *Actinomyces israelii*);

Brucella (e.g. *Brucella abortus, Brucella canis, Brucella melintensis* and *Brucella suis*);

Campylobacter (e.g. *Campylobacter jejuni, Campylobacter coil, Campylobacter fail* and *Campylobacter fetus*);

*Listeria monocytogenes;*

Vibrio (e.g. *Vibrio cholerae* and *Vibrio parahaemolyticus, Vibrio alginolyticus, Vibrio carchariae, Vibrio fluvialis, Vibrio furnissii, Vibrio hollisae, Vibrio metschnikovii, Vibrio mimicus* and *Vibrio vulnificus*);

*Erysipelothrix rhusopathiae;*

Corynebacteriaceae (e.g. *Corynebacterium diphtheriae, Corynebacterium jeikeum* and *Corynebacterium urealyticum*);

Spirochaetaceae, such as Borrelia (e.g. *Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukfi, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae* and *Borrelia venezuelensis*) and Treponema (*Treponema pallidum* ssp. *pallidum, Treponema pallidum* ssp. *endemicum, Treponema pallidum* ssp. *pertenue* and *Treponema carateum*);

Pasteurella (e.g. *Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida septica, Pasteurella pneumotropica* and *Pasteurella stomatis*);

Bordetella (e.g. *Bordetella bronchiseptica, Bordetella hinzii, Bordetella holmseii, Bordetella parapertussis, Bordetella pertussis* and *Bordetella trematum*);

Nocardiaceae, such as Nocardia (e.g. *Nocardia asteroides* and *Nocardia brasiliensis*);

Rickettsia (e.g. *Ricksettsii* or *Coxiella burnetii*);

Legionella (e.g. *Legionalla anisa, Legionalla birminghamensis, Legionalla bozemanii, Legionalla cincinnatiensis, Legionalla dumoffii, Legionalla feeleii, Legionalla gormanii, Legionalla hackeliae, Legionalla israelensis, Legionalla jordanis, Legionalla lansingensis, Legionalla longbeachae, Legionalla maceachemii, Legionalla micdadei, Legionalla oakridgensis, Legionalla pneumophila, Legionalla sainthelensi, Legionalla tucsonensis* and *Legionalla wadsworthii*);

*Moraxella catarrhalis;*

*Cyclospora cayetanensis;*

*Entamoeba histolytica;*

*Giardia lamblia;*

*Trichomonas vaginalis;*

*Toxoplasma gondii;*

*Stenotrophomonas maltophilia;*

*Burkholderia cepacia; Burkholderia mallei* and *Burkholderia pseudomallei;*

*Francisella tularensis;*

Gardnerella (e.g. *Gardneralla vaginalis* and *Gardneralla mobiluncus*); *Streptobacillus moniliformis;*

Flavobacteriaceae, such as Capnocytophaga (e.g. *Capnocytophaga canimorsus, Capnocytophaga cynodegmi, Capnocytophaga gingivalis, Capnocytophaga granulosa, Capnocytophaga haemolytica, Capnocytophaga ochracea* and *Capnocytophaga sputigena*);

Bartonella (*Bartonella bacilliformis, Bartonella clarridgeiae, Bartonella elizabethae, Bartonella henselae, Bartonella quintana* and *Bartonella vinsonii arupensis*);

Leptospira (e.g. *Leptospira biflexa, Leptospira borgpetersenii, Leptospira inadai, Leptospira interrogans, Leptospira kirschneri, Leptospira noguchii, Leptospira santarosai* and *Leptospira weilii*);

Spirillium (e.g. *Spirillum minus*);

Baceteroides (e.g. *Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus* and *Bacteroides vulgatus*);

Prevotella (e.g. *Prevotella bivia, Prevotella buccae, Prevotella corporis, Prevotella dentalis (Mitsuokella dentalis), Prevotella denticola, Prevotella disiens, Prevotella enoeca, Prevotella heparinolytica, Prevotella intermedia, Prevotella loeschii, Prevotella melaninogenica, Prevotella nigrescens, Prevotella oralis, Prevotella oris, Prevotella oulora, Prevotella tannerae, Prevotella venoralis* and *Prevotella zoogleoformans*);

Porphyromonas (e.g. *Porphyromonas asaccharolytica, Porphyromonas cangingivalis, Porphyromonas canoris, Porphyromonas cansulci, Porphyromonas catoniae, Porphyromonas circumdentaria, Porphyromonas crevioricanis, Por-* phyromonas endodontalis, *Porphyromonas gingivalis, Porphyromonas gingivicanis, Porphyromonas levii* and *Porphyromonas macacae*);

Fusobacterium (e.g. *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans* and *F. varium*);

Chlamydia (e.g. *Chlamydia trachomatis*);

Cryptosporidium (e.g. *C. parvum, C. hominis, C. canis, C. fells, C. meleagridis* and *C. muris*);

Chlamydophila (e.g. *Chlamydophila abortus* (*Chlamydia psittaci*), *Chlamydophila pneumoniae* (*Chlamydia pneumoniae*) and *Chlamydophila psittaci* (*Chlamydia psittaci*));

Leuconostoc (e.g. *Leuconostoc citreum, Leuconostoc cremoris, Leuconostoc dextranicum, Leuconostoc lactis, Leuconostoc mesenteroides* and *Leuconostoc pseudomesenteroides*);

Gemella (e.g. *Gemella bergeri, Gemella haemolysans, Gemella morbillorum* and *Gemella sanguinis*); and Ureaplasma (e.g. *Ureaplasma parvum* and *Ureaplasma urealyticum*).

As used herein, the term "fungi" (and derivatives thereof, such as "fungal infection") includes, but is not limited to, references to organisms (or infections due to organisms) of the following classes and specific types:

Absidia (e.g. *Absidia corymbifera*);

Ajellomyces (e.g. *Ajellomyces capsulatus* and *Ajellomyces dermatitidis*);

Arthroderma (e.g. *Arthroderma benhamiae, Arthroderma fulvum, Arthroderma gypseum, Arthroderma incurvatum, Arthroderma otae* and *Arthroderma vanbreuseghemii*);

Aspergillus (e.g. *Aspergillus flavus, Aspergillus fumigatus* and *Aspergillus niger*);

Blastomyces (e.g. *Blastomyces dermatitidis*);

Candida (e.g. *Candida albicans, Candida glabrata, Candida guilliermondii, Candida krusei, Candida parapsilosis, Candida tropicalis* and *Candida pelliculosa*);

Cladophialophora (e.g. *Cladophialophora carrionii*);

Coccidioides (e.g. *Coccidioides immitis* and *Coccidioides posadasii*);

Cryptococcus (e.g. *Cryptococcus neoformans*);

Cunninghamella (e.g. *Cunninghamella* sp.)

Epidermophyton (e.g. *Epidermophyton floccosum*);

Exophiala (e.g. *Exophiala dermatitidis*);

Filobasidiella (e.g. *Filobasidiella neoformans*);

Fonsecaea (e.g. *Fonsecaea pedrosoi*);

Fusarium (e.g. *Fusarium solani*);

Geotrichum (e.g. *Geotrichum candidum*);

Histoplasma (e.g. *Histoplasma capsulatum*);

Hortaea (e.g. *Hortaea werneckii*);

Issatschenkia (e.g. *Issatschenkia orientalis*);

Madurella (e.g. *Madurella grisae*);

Malassezia (e.g. *Malassezia furfur, Malassezia globosa, Malassezia obtusa, Malassezia pachydermatis, Malassezia restricta, Malassezia slooffiae* and *Malassezia sympodialis*);

Microsporum (e.g. *Microsporum canis, Microsporum fulvum* and *Microsporum gypseum*);

Microsporidia;

Mucor (e.g. *Mucor circinelloides*);

Nectria (e.g. *Nectria haematococca*);

Paecilomyces (e.g. *Paecilomyces variotii*);

Paracoccidioides (e.g. *Paracoccidioides brasiliensis*);

Penicillium (e.g. *Penicillium marneffei*);

Pichia (e.g. *Pichia anomala* and *Pichia guilliermondii*);

Pneumocystis (e.g. *Pneumocystis jiroveci* (*Pneumocystis carinii*));

Pseudallescheria (e.g. *Pseudallescheria boydii*);

Rhizopus (e.g. *Rhizopus oryzae*);

Rhodotorula (e.g. *Rhodotorula rubra*);

Scedosporium (e.g. *Scedosporium apiospermum*);

Schizophyllum (e.g. *Schizophyllum commune*);

Sporothrix (e.g. *Sporothrix schenckii*);

Trichophyton (e.g. *Trichophyton mentagrophytes, Trichophyton rubrum, Trichophyton verrucosum* and *Trichophyton violaceum*); and Trichosporon (e.g. *Trichosporon asahii, Trichosporon cutaneum, Trichosporon inkin* and *Trichosporon mucoides*).

Particular bacteria that may treated using a combination of the invention include:

Staphylococci, such as *Staph. aureus* (either Methicillin-sensitive (i.e. MSSA) or Methicillin-resistant (i.e. MRSA)) and *Staph. epidermidis*;

Streptococci, such as *Strept. agalactiae* and *Strept. pyogenes*;

Bacillaceae, such as *Bacillus anthracis*;

Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*);

Haemophilis influenzae;

Enterococci, such as *Enterococcus faecalis* and *Enterococcus faecium*; and

Mycobacteria, such as *Mycobacterium tuberculosis*.

Preferably, the bacterium is *S. aureus*; either MSSA or MRSA.

Particular fungi that may be treated with a combination of the invention include *Aspergillus fumigatus, Candida albicans, Cryptococcus neoformans, Histoplasma capsulatum* and *Pneumocystis jiroveci*.

The combinations of the present invention may be used to prevent and/or to treat infections associated with any bacterial or fungal organisms, such as those mentioned above; in particular, they may be used for killing multiplying, non-multiplying and/or clinically latent microorganisms associated with such an infection.

Particular conditions which may be prevented and/or treated using the combinations of the present invention include tuberculosis (e.g. pulmonary tuberculosis, non-pulmonary tuberculosis (such as tuberculosis lymph glands, genito-urinary tuberculosis, tuberculosis of bone and joints, tuberculosis meningitis) and miliary tuberculosis), anthrax, abscesses, acne vulgaris, actinomycosis, asthma, bacilliary dysentry, bacterial conjunctivitis, bacterial keratitis, bacterial vaginosis, botulism, Buruli ulcer, bone and joint infections, bronchitis (acute or chronic), brucellosis, burn wounds, cat scratch fever, cellulitis, chancroid, cholangitis, cholecystitis, cutaneous diphtheria, cystic fibrosis, cystitis, diffuse panbronchiolitis, diphtheria, dental caries, diseases of the upper respiratory tract, eczema, empymea, endocarditis, endometritis, enteric fever, enteritis, epididymitis, epiglottitis, erysipelis, erysipclas, erysipeloid, erythrasma, eye infections, furuncles, gardnerella vaginitis, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis (e.g. Madura foot), non-specific urethritis, opthalmia (e.g. opthalmia neonatorum), osteomyelitis, otitis (e.g. otitis externa and otitis media), orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma (e.g. impetigo), Q fever, rat-bite fever, reticulosis, ricin poisoning, Ritter's disease, salmonellosis, salpingitis, septic arthritis, septic infections, septicameia, sinusitis, skin infections (e.g. skin granulomas, impetigo, folliculitis and furunculosis), syphilis, systemic infections, tonsillitis, toxic shock syndrome, trachoma, tularaemia, typhoid, typhus (e.g. epidemic typhus, murine typhus, scrub typhus and spotted fever), urethritis, wound infections, yaws, aspergillosis, candidiasis (e.g. oropharyngeal candidiasis, vaginal candidiasis or balanitis), cryptococcosis, favus, histoplasmosis, intertrigo, mucormycosis, tinea (e.g. tinea corporis, tinea capitis, tinea cruris, tinea pedis and tinea unguium), onychomycosis, pityriasis versicolor, ringworm and sporotrichosis; or infections with MSSA, MRSA, *Staph. epidermidis*, *Strept. agalactiae*, *Strept. pyogenes*, *Escherichia coli*, *Klebs. pneumoniae*, *Klebs. oxytoca*, *Pr. mirabilis*, *Pr. rettgeri*, *Pr. vulgaris*, *Haemophilus influenzae*, *Enterococcus faecalis* and *Enterococcus faecium*.

References herein to "treatment" extend to prophylaxis as well as the treatment of established diseases or symptoms.

It will be appreciated that in one aspect of the present invention one or more additional antimicrobial compounds may also be administered with the above-mentioned combinations of the invention.

Suitable additional antimicrobial compounds for use in accordance with the combinations of the present invention include one or more compounds selected from the following:

(1) One or more additional beta-lactams, including:
  (i) penicillins, such as
    (I) benzylpenicillin, procaine benzylpenicillin, phenoxy-methylpenicillin, methicillin, propicillin, epicillin, cyclacillin, hetacillin, 6-aminopenicillanic acid, penicillic acid, penicillanic acid sulphone (sulbactam), penicillin G, penicillin V, phenethicillin, phenoxymethylpenicillinic acid, azlocillin, carbenicillin, cloxacillin, D-(−)-penicillamine, dicloxacillin, nafcillin and oxacillin,
    (II) penicillinase-resistant penicillins (e.g. flucloxacillin),
    (III) broad-spectrum penicillins (e.g. ampicillin, amoxicillin, metampicillin and bacampicillin),
    (IV) antipseudomonal penicillins (e.g. carboxypenicillins such as ticarcillin or ureidopenicillins such as piperacillin),
    (V) mecillinams (e.g. pivmecillinam), or
    (VI) combinations of any two or more of the agents mentioned at (I) to (V) above, or combinations of any of the agents mentioned at (I) to (V) above with a β-lactamase inhibitor such as tazobactam or, particularly, clavulanic acid (which acid is optionally in metal salt form, e.g. in salt form with an alkali metal such as sodium or, particularly, potassium);
  (ii) cephalosporins, such as cefaclor, cefadroxil, cefalexin (cephalexin), cefcapene, cefcapene pivoxil, cefdinir, cefditoren, cefditoren pivoxil, cefixime, cefotaxime, cefpirome, cefpodoxime, cefpodoxime proxetil, cefprozil, cefradine, ceftazidime, cefteram, cefteram pivoxil, ceftriaxone, cefuroxime, cefuroxime axetil, cephaloridine, cephacetrile, cephamandole, cephaloglycine, ceftobiprole, PPI-0903 (TAK-599), 7-aminocephalosporanic acid, 7-aminodes-acetoxycephalosporanic acid, cefamandole, cefazolin, cefmetazole, cefoperazone, cefsulodin, cephalosporin C zinc salt, cephalothin, cephapirin; and
  (iii) other β-lactams, such as monobactams (e.g. aztreonam), carbapenems (e.g. imipenem (optionally in combination with a renal enzyme inhibitor such as cilastatin), meropenem, ertapenem, doripenem (S-4661) and RO4908463 (CS-023)), penems (e.g. faropenem) and 1-oxa-β-lactams (e.g. moxalactam).

(2) Tetracyclines, such as tetracycline, demeclocycline, doxycycline, lymecycline, minocycline, oxytetracycline, chlortetracycline, meclocycline and methacycline, as well as glycylcyclines (e.g. tigecycline).

(3) Aminoglycosides, such as amikacin, gentamicin, netilmicin, neomycin, streptomycin, tobramycin, amastatin, butirosin, butirosin A, daunorubicin, dibekacin, dihydrostreptomycin, G 418, hygromycin B, kanamycin B, kanamycin, kirromycin, paromomycin, ribostamycin, sisomicin, spectinomycin, streptozocin and thiostrepton.

(4) (i) Macrolides, such as azithromycin, clarithromycin, erythromycin, roxithromycin, spiramycin, amphotericins B (e.g. amphotericin B), bafilomycins (e.g. bafilomycin A1), brefeldins (e.g. brefeldin A), concanamycins (e.g. concanamycin A), filipin complex, josamycin, mepartricin, midecamycin, nonactin, nystatin, oleandomycin, oligomycins (e.g. oligomycin A, oligomycin B and oligomycin C), pimaricin, rifampicin, rifamycin, rosamicin, tylosin, virginiamycin and fosfomycin.
  (ii) Ketolides such as telithromycin and cethromycin (ABT-773).
  (iii) Lincosamines, such as lincomycin.

(5) Clindamycin and clindamycin 2-phosphate.

(6) Phenicols, such as chloramphenicol and thiamphenicol.

(7) Steroids, such as fusidic acid (optionally in metal salt form, e.g. in salt form with an alkali metal such as sodium).

(8) Glycopeptides such as vancomycin, teicoplanin, bleomycin, phleomycin, ristomycin, telavancin, dalbavancin and oritavancin.

(9) Oxazolidinones, such as linezolid and AZD2563.

(10) Streptogramins, such as quinupristin and dalfopristin, or a combination thereof.

(11) (i) Peptides, such as polymyxins (e.g. colistin and polymyxin B), lysostaphin, duramycin, actinomycins (e.g. actinomycin C and actinomycin D), actinonin, 7-aminoactinomycin D, antimycin A, antipain, bacitracin, cyclosporin A, echinomycin, gramicidins (e.g. gramicidin A and gramicidin C), myxothiazol, nisin, paracelsin, valinomycin and viomycin.
  (ii) Lipopeptides, such as daptomycin.
  (iii) Lipoglycopeptides, such as ramoplanin.

(12) Sulfonamides, such as sulfamethoxazole, sulfadiazine, sulfaquinoxaline, sulfathiazole (which latter two agents are optionally in metal salt form, e.g. in salt form with an alkali metal such as sodium), succinylsulfathiazole, sulfadimethoxine, sulfaguanidine, sulfamethazine, sulfamonomethoxine, sulfanilamide and sulfasalazine.

(13) Trimethoprim, optionally in combination with a sulfonamide, such as sulfamethoxazole (e.g. the combination co-trimoxazole).

(14) Antituberculous drugs, such as isoniazid, rifampicin, rifabutin, pyrazinamide, ethambutol, streptomycin, amikacin, capreomycin, kanamycin, quinolones, para-aminosalicylic acid, cycloserine and ethionamide.

(15) Antileprotic drugs, such as dapsone, rifampicin and clofazimine.

(16) (i) Nitroimidazoles, such as metronidazole and tinidazole.
(ii) Nitrofurans, such as nitrofurantoin.
(17) Quinolones, such as nalidixic acid, norfloxacin, ciprofloxacin, ofloxacin, levofloxacin, moxifloxacin, gatifloxacin, gemifloxacin, garenoxacin, DX-619, WCK 771 (the arginine salt of S—(–)-nadifloxacin), 8-quinolinol, cinoxacin, enrofloxacin, flumequine, lomefloxacin, oxolinic acid and pipemidic acid.
(18) Amino acid derivatives, such as azaserine, bestatin, D-cycloserine, 1,10-phenanthroline, 6-diazo-5-oxo-L-norleucine and L-alanyl-L-1-aminoethyl-phosphonic acid.
(19) Aureolic acids, such as chromomycin A3, mithramycin A and mitomycin C.
(20) Benzochinoides, such as herbimycin A.
(21) Coumarin-glycosides, such as novobiocin.
(22) Diphenyl ether derivatives, such as irgasan.
(23) Epipolythiodixopiperazines, such as gliotoxin from *Gliocladium fimbriatum*.
(24) Fatty acid derivatives, such as cerulenin.
(25) Glucosamines, such as 1-deoxymannojirimycin, 1-deoxynojirimycin and N-methyl-1-deoxynojirimycin.
(26) Indole derivatives, such as staurosporine.
(27) Diaminopyrimidines, such as iclaprim (AR-100).
(28) Macrolactams, such as ascomycin.
(29) Taxoids, such as paclitaxel.
(30) Statins, such as mevastatin.
(31) Polyphenolic acids, such as (+)-usnic acid.
(32) Polyethers, such as lasalocid A, Ionomycin A, monensin, nigericin and salinomycin.
(33) Picolinic acid derivatives, such as fusaric acid.
(34) Peptidyl nucleosides, such as blasticidine S, nikkomycin, nourseothricin and puromycin.
(35) Nucleosides, such as adenine 9-β-D-arabinofuranoside, 5-azacytidine, cordycepin, formycin A, tubercidin and tunicamycin.
(36) Pleuromutilins, such as GSK-565154, GSK-275833 and tiamulin.
(37) Peptide deformylase inhibitors, such as LBM415 (NVP PDF-713) and BB 83698.
(38) Antibacterial agents for the skin, such as fucidin, benzamycin, clindamycin, erythromycin, tetracycline, silver sulfadiazine, chlortetracycline, metronidazole, framycitin, gramicidin, neomycin sulfate, polymyxins (e.g. polymixin B) and gentamycin.
(39) Miscellaneous agents, such as methenamine (hexamine), doxorubicin, piericidin A, stigmatellin, actidione, anisomycin, apramycin, coumermycin A1, L(+)-lactic acid, cytochalasins (e.g. cytochalasin B and cytochalasin D), emetine and ionomycin.
(40) Antiseptic agents, such as chlorhexidine, phenol derivatives (e.g. thymol and triclosan), quarternary ammonium compounds (e.g. benzalkonium chloride, cetylpyridinium chloride, benzethonium chloride, cetrimonium bromide, cetrimonium chloride and cetrimonium stearate), octenidine dihydrochloride, and terpenes (e.g. terpinen-4-ol).

In a preferred embodiment of the invention there is provided a combination comprising 4-methyl-8-phenoxy-1-(2-phenylethyl)-2,3-dihydro-1H-pyrrolo[3,2-c]quinoline or a pharmaceutically acceptable derivative thereof, chlorhexidine or a pharmaceutically acceptable derivative thereof, and an aminoglycoside antimicrobial agent.

Preferred aminoglycoside antimicrobial agents are amikacin, gentamicin, netilmicin, neomycin, streptomycin, tobramycin, amastatin, butirosin, butirosin A, daunorubicin, dibekacin, dihydrostreptomycin, G 418, hygromycin B, kanamycin B, kanamycin, kirromycin, paromomycin, ribostamycin, sisomicin, spectinomycin, streptozocin and thiostrepton, and pharmaceutically acceptable derivatives thereof. Particularly preferred glycosides are gentamicin and neomycin and pharmaceutically acceptable derivatives thereof, such as gentamicin sulphate and neomycin sulphate.

Thus, in one embodiment the present invention provides the use of 4-methyl-8-phenoxy-1-(2-phenylethyl)-2,3-dihydro-1H-pyrrolo[3,2-c]quinoline or a pharmaceutically acceptable derivative thereof in combination with chlorhexidine or a pharmaceutically acceptable derivative thereof, and an aminoglycoside antimicrobial agent for the prevention and/or treatment of a microbial infection; in particular for killing multiplying, non-multiplying and/or clinically latent microorganisms associated with such an infection.

As used herein the term "pharmaceutically acceptable derivative" means:
(a) pharmaceutically acceptable salts; and/or
(b) solvates (including hydrates).

Suitable acid addition salts include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalene-sulfonate or 1,5-naphthalenedisulfonate salts) or sulfate, pyrosulfate, bisulfate, sulfite, bisulfite, phosphate, monohydrogenphosphate, dihydrogenphosphate, metaphosphate, pyrophosphate or nitrate salts, and the like.

A preferred salt of mupirocin is the calcium salt thereof, i.e. mupirocin calcium.

Preferred salts of chlorhexidine are chlorhexidine digluconate, chlorhexidine gluconate, chlorhexidine hydrochloride, chlorhexidine dihydrochloride and chlorhexidine acetate, especially chlorhexidine gluconate.

For the avoidance of doubt, references herein to 4-methyl-8-phenoxy-1-(2-phenylethyl)-2,3-dihydro-1H-pyrrolo[3,2-c]quinoline mean a compound having the following chemical structure:

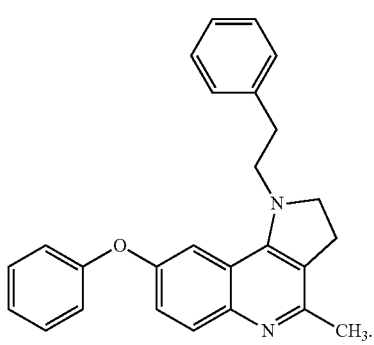 [SMILES: Cc1nc2ccc(Oc3ccccc3)cc2c2c1CCN2CCc1ccccc1]

4-methyl-8-phenoxy-1-(2-phenylethyl)-2,3-dihydro-1H-pyrrolo[3,2-c]quinoline or a pharmaceutically acceptable derivative thereof may be prepared by methods known in the art, for example by following the methods disclosed in International Patent Application, Publication Numbers WO2007054693 and WO2008056151. Preferred pharmaceutically acceptable derivatives of 4-methyl-8-phenoxy-1-(2-phenylethyl)-2,3-dihydro-1H-pyrrolo[3,2-c]quinoline include the hydrochloride and mesylate salts thereof.

Beta-lactam antimicrobial agents may be prepared according to known methods and/or are commercially available. For example, co-amoxiclav is commercially available from GlaxoSmithKline.

Mupirocin, mupirocin calcium and chlorhexidine are commercially available, for example from Sigma Aldrich Limited.

The compounds of the invention may be administered simultaneously or sequentially. When administered sequentially, 4-methyl-8-phenoxy-1-(2-phenylethyl)-2,3-dihydro-1H-pyrrolo[3,2-c]quinoline or a pharmaceutically acceptable derivative thereof or the other antimicrobial agent selected from the group consisting of a beta-lactam antimicrobial agent, mupirocin and chlorhexidine or a pharmaceutically acceptable derivative thereof, may be administered first. When administration is simultaneous, the combination may be administered either in the same or a different pharmaceutical composition.

The compounds of the invention may be administered as the raw material but the active ingredients are preferably provided in the form of pharmaceutical compositions.

The active ingredients may be used either as separate formulations or as a single combined formulation. When combined in the same formulation it will be appreciated that the compounds must be stable and compatible with each other and the other components of the formulation.

Formulations of the invention include those suitable for oral, parenteral (including subcutaneous e.g. by injection or by depot tablet, intradermal, intrathecal, intramuscular e.g. by depot and intravenous), rectal and topical (including dermal, buccal and sublingual) or in a form suitable for administration by inhalation or insufflation administration. The most suitable route of administration may depend upon the condition and disorder of the patient.

Preferably, the compositions of the invention are formulated for oral, topical or inhaled administration.

The formulations may conveniently be presented in unit dosage form and may be prepared by any of the methods well known in the art of pharmacy e.g. as described in *"Remington: The Science and Practice of Pharmacy"*, Lippincott Williams and Wilkins, 21$^{st}$ Edition, (2005). Suitable methods include the step of bringing into association to active ingredients with a carrier which constitutes one or more excipients. In general, formulations are prepared by uniformly and intimately bringing into association the active ingredients with liquid carriers or finely divided solid carriers or both and then, if necessary, shaping the product into the desired formulation. It will be appreciated that when the two active ingredients are administered independently, each may be administered by a different means.

When formulated with excipients, the active ingredients may be present in a concentration from 0.1 to 99.5% (such as from 0.5 to 95%) by weight of the total mixture; conveniently from 30 to 95% for tablets and capsules and 0.01 to 50% for liquid preparations.

A suitable concentration for 4-methyl-8-phenoxy-1-(2-phenylethyl)-2,3-dihydro-1H-pyrrolo[3,2-c]quinoline or a pharmaceutically acceptable derivative thereof is from about 0.1 to about 10%, preferably from about 0.1 to about 5%, for example 0.1, 0.25, 0.5, 0.75, 1, 2, 3, 4 or 5% by weight of the total mixture.

A suitable concentration for mupirocin or a pharmaceutically acceptable derivative thereof is from about 1 to about 5%, for example 1, 2, 3, 4 or 5%, preferably about 2% by weight of the total mixture.

A suitable concentration for chlorhexidine or a pharmaceutically acceptable derivative thereof is from about 0.01 to 5%, for example 0.01, 0.05, 0.1, 0.2, 0.3, 0.5, 0.75, 1, 2, 3, 4 or 5%, preferably about 0.2% by weight of the total mixture.

A suitable concentration for a beta-lactam such as co-amoxiclav is from about 0.01 to 10%, preferably from about 1 to 5% by weight of the total mixture.

Formulations suitable for oral administration may be presented as discrete units such as capsules, cachets or tablets (e.g. chewable tablets in particular for pediatric administration), each containing a predetermined amount of active ingredient; as powder or granules; as a solution or suspension in an aqueous liquid or non-aqueous liquid; or as an oil-in-water liquid emulsion or water-in-oil liquid emulsion. The active ingredients may also be presented a bolus, electuary or paste.

A tablet may be made by compression or moulding, optionally with one or more excipients. Compressed tablets may be prepared by compressing in a suitable machine the active ingredient in a free-flowing form such as a powder or granules, optionally mixed with other conventional excipients such as binding agents (e.g. syrup, acacia, gelatin, sorbitol, tragacanth, mucilage of starch, polyvinylpyrrolidone and/or hydroxymethyl cellulose), fillers (e.g. lactose, sugar, microcrystalline cellulose, maize-starch, calcium phosphate and/or sorbitol), lubricants (e.g. magnesium stearate, stearic acid, talc, polyethylene glycol and/or silica), disintegrants (e.g. potato starch, croscarmellose sodium and/or sodium starch glycolate) and wetting agents (e.g. sodium lauryl sulphate). Moulded tablets may be made by moulding in a suitable machine a mixture of the powdered active ingredient with an inert liquid diluent. The tablets may be optionally coated or scored and may be formulated so as to provide controlled release (e.g. delayed, sustained, or pulsed release, or a combination of immediate release and controlled release) of the active ingredients.

Alternatively, the active ingredients may be incorporated into oral liquid preparations such as aqueous or oily suspensions, solutions, emulsions, syrups or elixirs. Formulations containing the active ingredients may also be presented as a dry product for constitution with water or another suitable vehicle before use. Such liquid preparations may contain conventional additives such as suspending agents (e.g. sorbitol syrup, methyl cellulose, glucose/sugar syrup, gelatin, hydroxymethyl cellulose, carboxymethyl cellulose, aluminium stearate gel and/or hydrogenated edible fats), emulsifying agents (e.g. lecithin, sorbitan mono-oleate and/or acacia), non-aqueous vehicles (e.g. edible oils, such as almond oil, fractionated coconut oil, oily esters, propylene glycol and/or ethyl alcohol), and preservatives (e.g. methyl or propyl p-hydroxybenzoates and/or sorbic acid).

Topical compositions, which are useful for treating disorders of the skin or of membranes accessible by digitation (such as membrane of the mouth, vagina, cervix, anus and rectum), include creams, ointments, lotions, sprays, gels and sterile aqueous solutions or suspensions. As such, topical compositions include those in which the active ingredients are dissolved or dispersed in a dermatological vehicle known in the art (e.g. aqueous or non-aqueous gels, ointments, water-in-oil or oil-in-water emulsions). Constituents of such vehicles may comprise water, aqueous buffer solutions, non-aqueous solvents (such as ethanol, isopropanol, benzyl alcohol, 2-(2-ethoxyethoxy)ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed may contain one or more components selected from the following list: a solubilising agent or solvent (e.g. a β-cyclodextrin, such as hydroxypropyl β-cyclodextrin, or an alcohol or polyol such as ethanol, propylene glycol or glycerol); a thickening agent (e.g. hydroxymethyl cellulose, hydroxypropyl cellulose, carboxymethyl cellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (e.g. a mixture of dihydrogen phosphate and hydrogen phosphate salts, or a mixture of citric acid and a hydrogen phosphate salt). Topical formulations may also be formulated as a transdermal patch.

Methods of producing topical pharmaceutical compositions such as creams, ointments, lotions, sprays and sterile aqueous solutions or suspensions are well known in the art. Suitable methods of preparing topical pharmaceutical compositions are described, e.g. in WO9510999, U.S. Pat. No. 6,974,585, WO2006048747, as well as in documents cited in any of these references.

Topical pharmaceutical compositions according to the present invention may be used to treat a variety of skin or membrane disorders, such as infections of the skin or membranes (e.g. infections of nasal membranes, axilla, groin, perineum, rectum, dermatitic skin, skin ulcers, and sites of insertion of medical equipment such as i.v. needles, catheters and tracheostomy or feeding tubes) with any of the bacteria, fungi described above, (e.g. any of the *Staphylococci, Streptococci, Mycobacteria* or *Pseudomonas* organisms mentioned hereinbefore, such as *S. aureus* (e.g. Methicillin resistant *S. aureus* (MRSA))). In a preferred embodiment of the invention, there is provided a topical pharmaceutical composition for the nasal decolonisation of MRSA.

Topical compositions of the invention may be used for pre-operative surgical hand disinfection, antiseptic handwashing, and pre- and post-operative antisepsis for patients undergoing elective surgery.

Particular bacterial conditions that may be treated by topical pharmaceutical compositions of the present invention also include the skin- and membrane-related conditions disclosed hereinbefore, as well as: acne vulgaris; rosacea (including erythematotelangiectatic rosacea, papulopustular rosacea, phymatous rosacea and ocular rosacea); erysipelas; erythrasma; ecthyma; ecthyma gangrenosum; impetigo; paronychia; cellulitis; folliculitis (including hot tub folliculitis); furunculosis; carbunculosis; staphylococcal scalded skin syndrome; surgical scarlet fever; streptococcal peri-anal disease; streptococcal toxic shock syndrome; pitted keratolysis; trichomycosis axillaris; pyoderma; external canal ear infections; green nail syndrome; spirochetes; necrotizing fasciitis; Mycobacterial skin infections (such as lupus vulgaris, scrofuloderma, warty tuberculosis, tuberculides, erythema nodosum, erythema induratum, cutaneous manifestations of tuberculoid leprosy or lepromatous leprosy, erythema nodosum leprosum, cutaneous *M. kansasii, M. malmoense, M. szulgai, M. simiae, M. gordonae, M. haemophilum, M. avium, M. intracellulare, M. chelonae* (including *M. abscessus*) or *M. fortuitum* infections, swimming pool (or fish tank) granuloma, lymphadenitis and Buruli ulcer (Bairnsdale ulcer, Searles' ulcer, Kakerifu ulcer or Toro ulcer)); as well as infected eczema, burns, abrasions and skin wounds.

Particular fungal conditions that may be treated by topical pharmaceutical compositions of the present invention also include the skin- and membrane-related conditions disclosed hereinbefore, as well as: candidiasis; sporotrichosis; ringworm (e.g. tinea pedis, tinea cruris, tinea capitis, tinea unguium or tinea corporis); tinea versicolor; and infections with *Trichophyton, Microsporum, Epidermophyton* or *Pityrosporum* ovate fungi.

Compositions for use according to the invention may be presented in a pack or dispenser device which may contain one or more unit dosage forms containing the active ingredients. The pack may, e.g. comprise metal or plastic foil, such as a blister pack. Where the compositions are intended for administration as two separate compositions these may be presented in the form of a twin pack.

Pharmaceutical compositions may also be prescribed to the patient in "patient packs" containing the whole course of treatment in a single package, usually a blister pack. Patient packs have an advantage over traditional prescriptions, where a pharmacist divides a patients' supply of a pharmaceutical from a bulk supply, in that the patient always has access to the package insert contained in the patient pack, normally missing in traditional prescriptions. The inclusion of the package insert has been shown to improve patient compliance with the physician's instructions.

The administration of the combinations of the invention by means of a single patient pack, or patients packs of each composition, including a package insert directing the patient to the correct use of the invention is a further feature of this invention.

According to a further embodiment of the present invention there is provided a patient pack comprising at least one active ingredient of the combinations according to the invention, i.e. at least one of 4-methyl-8-phenoxy-1-(2-phenylethyl)-2,3-dihydro-1H-pyrrolo[3,2-c]quinoline or a pharmaceutically acceptable derivative thereof, a beta-lactam antimicrobial agent or a pharmaceutically acceptable derivative thereof, such as co-amoxiclav, mupirocin or a pharmaceutically acceptable derivative thereof, or chlorhexidine or a pharmaceutically acceptable derivative thereof, and an information insert containing directions on the use of the combination of the invention.

In another embodiment of the invention, there is provided a double pack comprising in association for separate administration, (a) 4-methyl-8-phenoxy-1-(2-phenylethyl)-2,3-dihydro-1H-pyrrolo[3,2-c]quinoline or a pharmaceutically acceptable derivative thereof, and (b) another antimicrobial agent selected from the group consisting of a beta-lactam antimicrobial agent (such as co-amoxiclav), mupirocin and chlorhexidine or a pharmaceutically acceptable derivative thereof.

The amount of active ingredients required for use in treatment will vary with the nature of the condition being treated and the age and condition of the patient, and will ultimately be at the discretion of the attendant physician or veterinarian. In general however, doses employed for adult human treatment will typically be in the range of 0.02 to 5000 mg per day, preferably 1 to 1500 mg per day. The desired dose may conveniently be presented in a single dose or as divided doses administered at appropriate intervals, e.g. as two, three, four or more sub-does per day. Suitable doses of co-amoxiclav are 375 (as 250 mg amoxicillin/125 mg potassium clavulanate) and 625 mg (as 500 mg amoxicillin/125 mg potassium clavulanate), administered up to three times per day.

Biological Tests

Test procedures that may be employed to determine the biological (e.g. bactericidal or antimicrobial) activity of the active ingredients include those known to persons skilled in the art for determining:
  (a) bactericidal activity against clinically latent bacteria; and
  (b) antimicrobial activity against log phase bacteria.

In relation to (a) above, methods for determining activity against clinically latent bacteria include a determination, under conditions known to those skilled in the art (such as those described in Nature Reviews, Drug Discovery 1, 895-910 (2002), the disclosures of which are hereby incorporated by reference), of Minimum Stationary-cidal Concentration ("MSC") or Minimum Dormicidal Concentration ("MDC") for a test compound.

By way of example, WO2000028074 describes a suitable method of screening compounds to determine their ability to kill clinically latent microorganisms. A typical method may include the following steps:
  (1) growing a bacterial culture to stationary phase;
  (2) treating the stationary phase culture with one or more antimicrobial agents at a concentration and or time sufficient to kill growing bacteria, thereby selecting a phenotypically resistant sub-population;
  (3) incubating a sample of the phenotypically resistant subpopulation with one or more test compounds or agents; and
  (4) assessing any antimicrobial effects against the phenotypically resistant subpopulation.

According to this method, the phenotypically resistant sub-population may be seen as representative of clinically latent bacteria which remain metabolically active in vivo and which can result in relapse or onset of disease.

In relation to (b) above, methods for determining activity against log phase bacteria include a determination, under standard conditions (i.e. conditions known to those skilled in the art, such as those described in WO2005014585, the disclosures of which document are hereby incorporated by reference), of Minimum Inhibitory Concentration (MIC) or Minimum Bactericidal Concentration (MBC) for a test compound. Specific examples of such methods are described below.

EXAMPLES

Materials and Methods

Bacterial Strains and Culture Medium

Staphylococcus aureus (Oxford); Gram positive; Reference strain.

Nutrient Broth No. 2 (NB) (Oxoid, Cambridge, UK) was used for overnight growth of bacteria.

Iso-Sensitest Broth (Oxoid) was used for evaluation of Minimum inhibitory concentrations (MICs), susceptibility tests for antimicrobials, and efficacy of antimicrobial combinations.

Trypton soya agar (TSA) (Oxoid, Cambridge, UK) was used for growth and quantification of organisms. All media were autoclaved at 121° C. for 15 minutes prior to use.

Bacterial Growth Conditions

Bacterial cultures were prepared by inoculation of 10 ml of nutrient broth with a single colony of bacteria on blood agar or TSA and incubated at 37° C. with continuous shaking at 100 rpm for 16 to 24 hours. The overnight cultures were used for experimental tests.

For CFU counting, the bacterial suspensions were diluted using sterile deionized water or phosphate-buffered saline (PBS, Sigma Aldrich Ltd, Poole, Dorset, UK). 100 µl of 10-fold serial dilutions of bacteria culture were plated on one third of TSA plates in triplicate and incubated 24 to 48 hours at 37° C. The number of cells presented on the plates was counted using an AcoLyte colony counter (Synbiosis) and results were expressed as Colony Forming Units/ml (CFU/ml).

Antibiotics

Co-amoxiclav (1000/200 mg infusion, GlaxoSmithKline) was purchased from St George's NHS Hospital, London. Mupirocin was purchased from Sigma Aldrich Ltd (Poole, Dorset, UK). Chlorhexidine gluconate was purchased from Sigma Aldrich Ltd (Poole, Dorset, UK). 4-methyl-8-phenoxy-1-(2-phenylethyl)-2,3-dihydro-1H-pyrrolo[3,2-c] quinoline (in hydrochloride salt form) was provided by Helperby Therapeutics.

Stocks of 10 mg/ml of each of the antibiotics were prepared by dilution in dimethyl sulfoxide (DMSO) or water respectively. The antibiotic solutions were stored at −20° C.

Evaluation of MIC and MBC

Minimum inhibitory concentration (MIC) analyses for co-amoxiclav, mupirocin, chlorhexidine and 4-methyl-8-phenoxy-1-(2-phenylethyl)-2,3-dihydro-1H-pyrrolo[3,2-c] quinoline were performed in Iso-Sensitest broth using a broth dilution method and were determined as the lowest concentration of antimicrobial agent that inhibited visible growth after overnight incubation at 37° C. The stock solution of each drug was diluted to required concentrations. 10 µl of drug from each dilution was taken and mixed with 290 µl of culture with $10^6$ of bacterial cells on a 96-well plate to make the final required concentrations (µg/ml).

The plates were read at 405 nm using a 96-well plate reader Elx 800 equipped with a 405-nm filter (Bio-Tek) before and after incubation. The MIC values of the drugs were determined by comparison of the optical density reading between prior and post drug treatment.

Minimum bactericidal concentration (MBC) was determined by subculturing 100 µl of dilutions from the 96-well plate on fresh drug-free TSA agar plates and incubating further for 24 to 48 hours at 37° C. The highest dilution that showed no single bacterial colony on TSA plates was taken as the MBC.

Efficacy of Antimicrobial Combinations

The antimicrobial activity of 4-methyl-8-phenoxy-1-(2-phenylethyl)-2,3-dihydro-1H-pyrrolo[3,2-c]quinoline in combination with (a) co-amoxiclav; (b) mupirocin; and (c) chlorhexidine gluconate against S. aureus, in a concentration range from below to above the MIC, was assessed in a suspension assay by the time-kill curve method.

(a) 4-methyl-8-phenoxy-1-(2-phenylethyl)-2,3-dihydro-1H-pyrrolo[3,2-c]quinoline in combination co-amoxiclav Serial double dilutions of the antimicrobial compounds were prepared: 4-methyl-8-phenoxy-1-(2-phenylethyl)-2,3- dihydro-1H-pyrrolo[3,2-c]quinoline from 16 µg/ml to 0.25 µg/ml; and co-amoxiclav from 2 to 0.03 µg/ml. Ten microliters of each antimicrobial solution were added to the rows of a 96-well microtitre plate in diminishing concentrations, and then 10 µl of 4-methyl-8-phenoxy-1-(2-phenylethyl)-2,3-dihydro-1H-pyrrolo[3,2-c]quinoline was added to the columns in decreasing concentrations. The wells were then inoculated with 280 µl of S. aureus (Oxford strain) suspension containing $10^7$ CFU/ml of inocula. Drug free controls were also included.

The microtitre plates were incubated at 37° C. for 16 to 24 hours, read in a 96-well plate reader, then samples were diluted and 100 µl of each dilution was plated out on TSA plates. After 24 to 48 hours incubation CFU was counted. Each test was performed in triplicate and repeated twice. Synergy was defined as a 2 $\log_{10}$ decrease in colony counts, when antibacterial activity of combinations was compared with that of the most active single agent.

(b) 4-methyl-8-phenoxy-1-(2-phenylethyl)-2,3-dihydro-1H-pyrrolo[3,2-c]quinoline in combination with mupirocin Serial double dilutions of the antimicrobial compounds were prepared: 4-methyl-8-phenoxy-1-(2-phenylethyl)-2,3-dihydro-1H-pyrrolo[3,2-c]quinoline from 16 µg/ml to 0.25 µg/ml; and mupirocin from 40 to 0.03 µg/ml. Ten microliters of each antimicrobial solution were added to the rows of a 96-well microtitre plate in diminishing concentrations, and then 10 µl of 4-methyl-8-phenoxy-1-(2-phenylethyl)-2,3-dihydro-1H-pyrrolo[3,2-c]quinoline was added to the columns in decreasing concentrations. The wells were then inoculated with 280 µl of S. aureus (Oxford strain) suspension containing $10^7$ CFU/ml of inocula. Drug free controls were also included.

The microtitre plates were incubated at 37° C. for 16 to 24 hours, read in a 96-well plate reader, then samples were diluted and 100 µl of each dilution was plated out on TSA plates. After 24 to 48 hours incubation CFU was counted. In addition for combination of 4-methyl-8-phenoxy-1-(2-phenylethyl)-2,3-dihydro-1H-pyrrolo[3,2-c]quinoline with mupirocin (4-methyl-8-phenoxy-1-(2-phenylethyl)-2,3-dihydro-1H-pyrrolo[3,2-c]quinoline: 10, 8, 4 µg/ml; mupirocin: 40, 20, 10 µg/ml) samples were plated out immediately after procedure and after 4, 6, 24, 48, 72, 96, 168 hours of incubation. Each test was performed in triplicate and repeated twice. Synergy was defined as a 2 $\log_{10}$ decrease in colony counts, when antibacterial activity of combinations was compared with that of the most active single agent.

(c) 4-methyl-8-phenoxy-1-(2-phenylethyl)-2,3-dihydro-1H-pyrrolo[3,2-c]quinoline in combination with chlorhexidine Serial double dilutions of the antimicrobial compounds were prepared: 4-methyl-8-phenoxy-1-(2-phenylethyl)-2,3-dihydro-1H-pyrrolo[3,2-c]quinoline from 16 µg/ml to 0.25 µg/ml; and chlorhexidine gluconate from 16 to 0.25 µg/ml. Ten microliters of each antimicrobial solution were added to the rows of a 96-well microtitre plate in diminishing concentrations, and then 10 µl of 4-methyl-8-phenoxy-1-(2-phenylethyl)-2,3-dihydro-1H-pyrrolo[3,2-c]quinoline was added to the columns in decreasing concentrations. The wells were then inoculated with 280 µl of S. aureus (Oxford strain) suspensions containing $10^7$ or $10^8$ and CFU/ml of inocula. Drug free controls were also included.

The microtitre plates were incubated at 37° C. for 16 to 24 hours, read in a 96-well plate reader, then samples were diluted and 100 µl of each dilution was plated out on TSA plates. After 24 to 48 hours incubation CFU was counted. Each test was performed in triplicate and repeated twice. Synergy was defined as a 2 $\log_{10}$ decrease in colony counts, when antibacterial activity of combinations was compared with that of the most active single agent.

Statistical Analyses

The mean bacterial colony count at varying time points was compared by the two-tailed t-test with unequal variance. P values of ≤0.05 indicated significant difference.

Results (1) 4-methyl-8-phenoxy-1-(2-phenylethyl)-2,3-dihydro-1H-pyrrolo[3,2-c]quinoline/Co-Amoxiclav Combination Determination of Susceptibility of S. Aureus to Co-Amoxiclav and 4-methyl-8-phenoxy-1-(2-phenylethyl)-2,3-dihydro-1H-pyrrolo[3,2-c]quinoline

| Antimicrobial agent | MIC (µg/ml) | MBC (µg/ml) |
|---|---|---|
| Co-amoxiclav | 0.125 | — |
| 4-methyl-8-phenoxy-1-(2-phenylethyl)-2,3-dihydro-1H-pyrrolo[3,2-c]quinoline | 8 | 16 |

Time-Kill Studies for 4-methyl-8-phenoxy-1-(2-phenylethyl)-2,3-dihydro-1H-pyrrolo[3,2-c]quinoline in Combination with Co-Amoxiclav The kill curve results for a combination of 4-methyl-8-phenoxy-1-(2-phenylethyl)-2,3-dihydro-1H-pyrrolo[3,2-c]quinoline (4 µg/ml) with co-amoxiclav against S. aureus are shown in FIG. 1. Results are displayed as means of log reduction in viable organisms±standard deviation (*P<0.0001). The growth control for these experiments is not shown but was grossly turbid during the time of experiments.

(2) 4-methyl-8-phenoxy-1-(2-phenylethyl)-2,3-dihydro-1H-pyrrolo[3,2-c]quinoline/Mupirocin Combination Determination of Susceptibility of S. Aureus to Mupirocin and 4-methyl-8-phenoxy-1-2-phenylethyl)-2,3-dihydro-1H-pyrrolo[3,2-c]quinoline

| Antimicrobial agent | MIC (µg/ml) | MBC (µg/ml) |
|---|---|---|
| Mupirocin | 0.125 | 256 |
| 4-methyl-8-phenoxy-1-(2-phenylethyl)-2,3-dihydro-1H-pyrrolo[3,2-c]quinoline | 8 | 16 |

Time-Kill Studies for 4-methyl-8-phenoxy-1-(2-phenylethyl)-2,3-dihydro-1H-pyrrolo[3,2-c]quinoline in Combination with Mupirocin The killing profiles of combinations of 4-methyl-8-phenoxy-1-(2-phenylethyl)-2,3-dihydro-1H-pyrrolo[3,2-c]quinoline with mupirocin against S. aureus are shown in FIGS. 2 to 10. Asterisks indicate a significant difference (*P<0.05,P<0.001,*P<0.0001) in CFU count between the combination of drugs and drugs alone (FIGS. 2 to 7 are compared to 4-methyl-8-phenoxy-1-(2-phenylethyl)-2,3-dihydro-1H-pyrrolo[3,2-c]quinoline alone, FIGS. 8 to 10 are compared to mupirocin alone). The growth control for these experiments is not shown but was grossly turbid during the time of experiments.

A consistent trend was apparent for the combination of 10 and 8 µg/ml 4-methyl-8-phenoxy-1-(2-phenylethyl)-2,3-dihydro-1H-pyrrolo[3,2-c]quinoline with all concentrations of mupirocin (40, 20, 10 µg/ml). Those combinations were found to be synergistic after 48 hours of incubation (P<0.05 for all combinations of 4-methyl-8-phenoxy-1-(2-phenylethyl)-2,3-dihydro-1H-pyrrolo[3,2-c]quinoline (10 µg/ml) with mupirocin; P<0.0001 for 4-methyl-8-phenoxy-1-(2-phenylethyl)-2,3-dihydro-1H-pyrrolo[3,2-c]quinoline (8 µg/ml) with mupirocin).

In contrast, a lower dose of 4-methyl-8-phenoxy-1-(2-phenylethyl)-2,3-dihydro-1H-pyrrolo[3,2-c]quinoline (4 µg/ml) with mupirocin had a lower impact on the growth of S. aureus. However, synergy was still observed for these combinations at 168 hours in comparison to 4-methyl-8-phenoxy-1-(2-phenylethyl)-2,3-dihydro-1H-pyrrolo[3,2-c]quinoline or mupirocin alone (FIGS. 8 to 10). These differences in rate of killing were highly statistical significant (P<0.0001).

FIG. 11 shows the difference in bacterial killing between the combination of 4-methyl-8-phenoxy-1-(2-phenylethyl)-2,3-dihydro-1H-pyrrolo[3,2-c]quinoline (5 µg/ml) and mupirocin, compared to 4-methyl-8-phenoxy-1-(2-phenylethyl)-2,3-dihydro-1H-pyrrolo[3,2-c]quinoline and mupirocin alone. Results are displayed as means of log reduction in viable organisms±standard deviation (P<0.05).

(3) 4-methyl-8-phenoxy-1-(2-phenylethyl)-2,3-dihydro-1H-pyrrolo[3,2-c]quinoline/Chlorhexidine Gluconate Combination Determination of Susceptibility of S. Aureus to Chlorhexidine Gluconate and 4-methyl-8-phenoxy-1-(2-phenylethyl)-2,3-dihydro-1H-pyrrolo[3,2-c]quinoline

| Antimicrobial agent | MIC (µg/ml) | MBC (µg/ml) |
|---|---|---|
| Chlorhexidine gluconate | 0.5 | 2 |
| 4-methyl-8-phenoxy-1-(2-phenylethyl)-2,3-dihydro-1H-pyrrolo[3,2-c]quinoline | 8 | 16 |

Time-Kill Studies for 4-methyl-8-phenoxy-1-(2-phenylethyl)-2,3-dihydro-1H-pyrrolo[3,2-c]quinoline in Combination With Chlorhexidine Gluconate The killing profile of 4-methyl-8-phenoxy-1-(2-phenylethyl)-2,3-dihydro-1H-pyrrolo[3,2-c]quinoline (5 µg/ml) in combination with chlorhexidine gluconate against S. aureus is shown in FIG. 12. The growth control for these experiments is not shown but was grossly turbid during the time of experiments.

FIGS. 13 and 14 show the differences in bacterial killing between combinations of 4-methyl-8-phenoxy-1-(2-phenylethyl)-2,3-dihydro-1H-pyrrolo[3,2-c]quinoline (5 and 4 µg/ml) and chlorhexidine gluconate (0.5 and 1 µg/ml), compared to 4-methyl-8-phenoxy-1-(2-phenylethyl)-2,3-dihydro-1H-pyrrolo[3,2-c]quinoline and chlorhexidine gluconate alone.

Results are displayed as means of log reduction in viable organisms±standard deviation (P<0.001,*P<0.0001).

Conclusions 4-methyl-8-phenoxy-1-(2-phenylethyl)-2,3-dihydro-1H-pyrrolo[3,2-c]quinoline at 4 µg/ml showed no activities against log phase S. aureus. Co-amoxiclav at 0.5 and 0.25 µg/ml reduced 3 and 2 logs of CFU counts, respectively.

However, 4-methyl-8-phenoxy-1-(2-phenylethyl)-2,3-dihydro-1H-pyrrolo[3,2-c]quinoline (4 µg/ml) in combination with 0.5 and 0.25 µg/ml co-amoxiclav further reduced CFU counts to 3.5 log and 1.5 log respectively. Significant synergistic activities were thus observed when 4-methyl-8-phenoxy-1-(2-phenylethyl)-2,3-dihydro-1H-pyrrolo[3,2-c]quinoline was combined with co-amoxiclav.

Mupirocin alone was bacteriostatic which showed slow activity against log phase S. aureus at 40, 20 and 10 µg/ml. 4-methyl-8-phenoxy-1-(2-phenylethyl)-2,3-dihydro-1H-pyrrolo[3,2-c]quinoline showed bactericidal activity at 10 and 8 µg/ml which reduced $10^7$ CFU/ml to zero at 72 hours. 4-methyl-8-phenoxy-1-(2-phenylethyl)-2,3-dihydro-1H-pyrrolo[3,2-c]quinoline at 4 µg/ml showed no activity against the same bacterial culture.

However, combinations of 4-methyl-8-phenoxy-1-(2-phenylethyl)-2,3-dihydro-1H-pyrrolo[3,2-c]quinoline and mupirocin at different concentrations demonstrated a significant synergistic activity against S. aureus. For example, 4-methyl-8-phenoxy-1-(2-phenylethyl)-2,3-dihydro-1H-pyrrolo[3,2-c]quinoline at 10 µg/ml in combination with mupirocin at 40, 20 and 10 µg/ml reduced the CFU counts to 0 at 48 hours. Significant synergistic activities were also seen with combination of 4-methyl-8-phenoxy-1-(2-phenylethyl)-2,3-dihydro-1H-pyrrolo[3,2-c]quinoline at 8 and 4 µg/ml and mupriocin 40, 20 and 10 µg/ml.

The results of the kill curve study given in FIG. 12 show a 3 log higher rate of killing (P<0.05) for 4-methyl-8-phenoxy-1-(2-phenylethyl)-2,3-dihydro-1H-pyrrolo[3,2-c]quinoline (5 µg/ml) in combination with chlorhexidine gluconate (5 µg/ml), compared to chlorhexidine gluconate alone.

The results given in FIGS. 13 and 14 show highly significant differences (P<0.0001) between the mean logarithmic reductions achieved with 4-methyl-8-phenoxy-1-(2-phenylethyl)-2,3-dihydro-1H-pyrrolo[3,2-c]quinoline in combination with chlorhexidine gluconate, compared to chlorhexidine alone. Synergistic reductions (range of 2.5 to 4.5 log) in CFU/ml were observed for all combinations compared to controls.

In Vitro Activity of 4-methyl-8-phenoxy-1-(2-phenylethyl)-2,3-dihydro-1H-pyrrolo[3,2-c]quinoline in Combination with Chlorhexidine Against Stationary Phase Staphylococcus aureus (MSSA and MRSA) by CFU Counts Bacterial Strains Staphylococcus aureus (Oxford); Gram positive; Reference strain.

MRSA—clinical isolate provided by Medical Microbiology, St George's NHS, London.

Bacterial Growth Conditions

A single colony of S. aureus or MRSA was inoculated in 10 ml of nutrient broth No. 2 (NB, Oxoid) which was incubated overnight at 37° C. with continuous shaking at 120 rpm. 200 µl of the overnight culture was added into a 500 ml screw cap bottle which contained 100 ml of NB. The 100 ml culture was incubated at 37° C. with continuous shaking for 5 days.

Antibiotics

Chlorhexidine was purchased from Sigma Aldrich Ltd. 4-methyl-8-phenoxy-1-(2-phenylethyl)-2,3-dihydro-1H-pyrrolo[3,2-c]quinoline (in mesylate salt form) was provided by Helperby Therapeutics.

Stocks of 10 mg/ml of 4-methyl-8-phenoxy-1-(2-phenylethyl)-2,3-dihydro-1H-pyrrolo[3,2-c]quinoline mesylate and 200 mg/ml of chlorhexidine were prepared by dilution in water. The antibiotic solutions were stored at −20° C.

5 day stationary phase bacterial culture was diluted using phosphate buffered saline (PBS) to $10^7$ CFU/ml. The stationary phase cell suspension was incubated with 4-methyl-8-phenoxy-1-(2-phenylethyl)-2,3-dihydro-1H-pyrrolo[3,2-c]quinoline, chlorhexidine and the drug combination. Incubation of the compounds with the bacterial suspension was carried out for 8 hours. At 2 hour intervals, CFU counts were performed in accordance with the method described above.

Results

The kill curve results for combinations of 4-methyl-8-phenoxy-1-(2-phenylethyl)-2,3-dihydro-1H-pyrrolo[3,2-c]quinoline mesylate (HT61) (8, 4 or 2 µg/ml) with chlorhexidine (CHD) (8, 4 or 2 µg/ml) against MRSA are shown in FIGS. 15 to 20 and against MSSA in FIGS. 21 to 28. Results are displayed as means of log reduction in viable organisms±standard deviation (*$P<0.005$, $P<0.001$ and *$P<0.0001$).

Conclusions

Synergistic antimicrobial activity was observed for combinations of 4-methyl-8-phenoxy-1-(2-phenylethyl)-2,3-dihydro-1H-pyrrolo[3,2-c]quinoline mesylate (8, 4 or 2 µg/ml) with chlorhexidine (CHD) (8, 4 or 2 µg/ml) against stationery phase MSSA and MRSA.

The invention claimed is:

1. A combination comprising 4-methyl-8-phenoxy-1-(2-phenylethyl)-2,3-dihydro-1H-pyrrolo[3,2-c]quinoline or a pharmaceutically acceptable derivative thereof and another antimicrobial agent selected from the group consisting of a beta-lactam antimicrobial agent, mupirocin and chlorhexidine or a pharmaceutically acceptable derivative thereof.

2. A combination according to claim 1 comprising 4-methyl-8-phenoxy-1-(2-phenylethyl)-2,3-dihydro-1H-pyrrolo[3,2-c]quinoline or a pharmaceutically acceptable derivative thereof and a beta-lactam antimicrobial agent or a pharmaceutically acceptable derivative thereof.

3. A combination according to claim 2 wherein the beta-lactam antimicrobial agent is co-amoxiclav.

4. A combination according to claim 1 comprising 4-methyl-8-phenoxy-1-(2-phenylethyl)-2,3-dihydro-1H-pyrrolo[3,2-c]quinoline or a pharmaceutically acceptable derivative thereof and mupirocin or a pharmaceutically acceptable derivative thereof.

5. A combination according to claim 1 comprising 4-methyl-8-phenoxy-1-(2-phenylethyl)-2,3-dihydro-1H-pyrrolo[3,2-c]quinoline or a pharmaceutically acceptable derivative thereof and chlorhexidine or a pharmaceutically acceptable derivative thereof.

6. A combination according to claim 5 further comprising an aminoglycoside antimicrobial agent.

7. A combination according to claim 6 wherein the aminoglycoside is gentamicin, neomycin or a pharmaceutically acceptable derivative thereof.

8. A combination according to claim 1 for use in the prevention and/or treatment of a microbial infection.

9. A combination according to claim 8 for use in killing multiplying microorganisms associated with a microbial infection.

10. A combination according to claim 8 for use in killing non-multiplying microorganisms associated with a microbial infection.

11. A combination according to claim 8 for use in killing clinically latent microorganisms associated with a microbial infection.

12. A method of manufacturing a medicament comprising combining 4 methyl-8-phenoxy-1-(2-phenylethyl)-2,3-dihydro-1H-pyrrolo[3,2-c]quinoline or a pharmaceutically acceptable derivative thereof with another antimicrobial agent selected from the group consisting of a beta-lactam antimicrobial agent, mupirocin and chlorhexidine or a pharmaceutically acceptable derivative thereof.

13. A method of treating a microbial infection comprising administering to a patient a combination of 4 methyl-8-phenoxy-1-(2-phenylethyl)-2,3-dihydro-1H-pyrrolo[3,2-c]quinoline or a pharmaceutically acceptable derivative thereof and another antimicrobial agent selected from the group consisting of a beta-lactam antimicrobial agent, mupirocin and chlorhexidine or a pharmaceutically acceptable derivative thereof.

14. The method according to claim 13 wherein the infection is a bacterial infection.

15. The method according to claim 14 wherein the infection is caused by *Staphylococci, Streptococci, Bacillaceae, Enterobacteriaceae, Haemophilis influenzae, Enterococci, Mycobacteria*.

16. The method according to claim 15 wherein the infection is caused by *Staphylococcus aureus*.

17. The method according to claim 13 wherein the microbial infection is a fungal infection.

18. The method according to claim 17 wherein the infection is caused by *Aspergillus fumigatus, Candida albicans, Cryptococcus neoformans, Histoplasma capsulatum* and *Pneumocystis jiroveci*.

19. The method according to claim 13 wherein the treatment is of tuberculosis, anthrax, abscesses, acne vulgaris, actinomycosis, asthma, bacilliary dysentry, bacterial conjunctivitis, bacterial keratitis, bacterial vaginosis, botulism, Buruli ulcer, bone and joint infections, bronchitis (acute or chronic), brucellosis, burn wounds, cat scratch fever, cellulitis, chancroid, cholangitis, cholecystitis, cutaneous diphtheria, cystic fibrosis, cystitis, diffuse panbronchiolitis, diphtheria, dental caries, diseases of the upper respiratory tract, eczema, empymea, endocarditis, endometritis, enteric fever, enteritis, epididymitis, epiglottitis, erysipelis, erysipclas, erysipeloid, erythrasma, eye infections, furuncles, gardnerella vaginitis, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis, non-specific urethritis, opthalmia, osteomyelitis, otitis, orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma, Q fever, rat-bite fever, reticulosis, ricin poisoning, Ritter's disease, salmonellosis, salpingitis, septic arthritis, septic infections, septicameia, sinusitis, skin infections, syphilis, systemic infections, tonsillitis, toxic shock syndrome, trachoma, tularaemia, typhoid, typhus, urethritis, wound infections, yaws, aspergillosis, candidiasis, cryptococcosis, favus, histoplasmosis, intertrigo, mucormycosis, tinea, onychomycosis, pityriasis versicolor, ringworm and sporotrichosis; or infections with MSSA, MRSA, *Staph. epidermidis, Strept. agalactiae, Strept. pyogenes, Escherichia coli, Klebs. pneumoniae, Klebs. oxytoca, Pr. mirabilis, Pr. rettgeri, Pr. vulgaris, Haemophilis influenzae, Enterococcus faecalis* and *Enterococcus faecium*.

20. A pharmaceutical composition comprising 4-methyl-8-phenoxy-1-(2-phenylethyl)-2,3-dihydro-1H-pyrrolo[3,2-c]quinoline or a pharmaceutically acceptable derivative thereof, another antimicrobial agent selected from the group consisting of a beta-lactam antimicrobial agent, mupirocin and chlorhexidine or a pharmaceutically acceptable derivative thereof, and a pharmaceutically acceptable adjuvant, diluent or carrier.

21. A pharmaceutical composition according to claim 20 which is formulated for oral, inhaled or topical administration.

22. A product comprising 4-methyl-8-phenoxy-1-(2-phenylethyl)-2,3-dihydro-1H-pyrrolo[3,2-c]quinoline or a pharmaceutically acceptable derivative thereof and another antimicrobial agent selected from the group consisting of a beta-lactam antimicrobial agent, mupirocin and chlorhexidine or a pharmaceutically acceptable derivative thereof, as a combined preparation for simultaneous, separate or sequential use in the treatment of a microbial infection.

\* \* \* \* \*